US008679790B2

(12) United States Patent
Plotkin et al.

(10) Patent No.: US 8,679,790 B2
(45) Date of Patent: Mar. 25, 2014

(54) LEADER SEQUENCE TO BOOST GENE EXPRESSION

(75) Inventors: Joshua B. Plotkin, Philadelphia, PA (US); Grzegorz Kudla, Edinburgh (GB)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 464 days.

(21) Appl. No.: 12/984,251

(22) Filed: Jan. 4, 2011

(65) Prior Publication Data

US 2011/0217778 A1    Sep. 8, 2011

Related U.S. Application Data

(60) Provisional application No. 61/292,366, filed on Jan. 5, 2010.

(51) Int. Cl.
| | |
|---|---|
| C12N 15/113 | (2010.01) |
| C12N 15/09 | (2006.01) |
| C12N 15/63 | (2006.01) |
| C12N 15/64 | (2006.01) |
| C12N 15/66 | (2006.01) |
| C12N 15/67 | (2006.01) |
| C12N 5/10 | (2006.01) |
| C07H 21/02 | (2006.01) |
| C07H 21/04 | (2006.01) |

(52) U.S. Cl.
USPC ....... 435/91.41; 435/69.1; 435/455; 435/325; 435/320.1; 435/91.1; 435/91.4; 435/810; 536/23.1; 536/24.1; 536/25.3

(58) Field of Classification Search
USPC .............. 536/23.1, 24.1, 25.3; 435/69.1, 455, 435/325, 320.1, 91.1, 91.4, 91.41, 810
See application file for complete search history.

(56) References Cited

PUBLICATIONS

Kudla, G., et al. Science, 234: 255-258, Apr. 10, 2009.*
Andersson et al., "Codon preferences in free-living microorganisms." 1990 Microbial. Rev. 54(2): 198-210.
Boycheva et al., "Codon pairs in the genome of *Escherichia coli*." 2003 Bioinformatics 19(8): 987-98.
Coleman et al., "Virus attenuation by genome-scale changes in codon pair bias." 2008 Science 320(5884):1784-7.
Drummond et al., "Why highly expressed proteins evolve slowly." 2005 Proc. Natl. Acad. Sci. U.S.A. 102(40): 14338-43.
Eyre-Walker et al., "Reduced synonymous substitution rate at the start of enterobacterial genes." 1993 Nucleic Acids Res. 21(19): 4599-4603.
Gonzalez De Valdivia et al., "A codon window in mRNA downstream of the initiation codon where NGG codons give strongly reduced gene expression in *Escherichia coli*." 2004 Nucleic Acids Res. 32(17): 5198-5205.
Gustafsson et al., "Codon bias and heterologous protein expression." 2004 Trends Biotechnol. 22(7): 346-353.
Ikemura, "Correlation between the abundance of *Escherichia coil* transfer RNAs and the occurrence of the respective codons in its protein genes: a proposal for a synonymous codon choice that is optimal for the *E. coli* translational system." 1981 J. Mol. Biol. 151(3): 389-409.
Kimchi-Sarfaty et al., "A "silent" polymorphism in the MDR1 gene changes substrate specificity." 2007 Science 315(5811): 525-8.
Lithwick et al., "Hierarchy of sequence-dependent features associated with prokaryotic translation." 2003 Genome Res. 13(12): 2665-2673.
Nackley et al., "Human catechol-O-methyltransferase haplotypes modulate protein expression by altering mRNA secondary structure." 2006 Science 314(5807): 1930-1933.
Parmley et al., "How do synonymous mutations affect fitness?" 2007 Bioessays 29(6): 515-519.
Plotkin, et al., "Assessing the determinants of evolutionary rates in the presence of noise." 2007, Mol Biol Evol 24(5):1113-1121.
Rosenberg et al., "Effects of consecutive AGG codons on translation in *Escherichia coli*, demonstrated with a versatile codon test system." 1993 J. Bacteriol. 175(3): 716-22.
Sharp et al., "The codon Adaptation Index—a measure of directional synonymous codon usage bias, and its potential applications." 1987 Nucleic Acids Res. 15(3): 1281-1295.
Stoletzki et al., "Synonymous codon usage in *Escherichia coli*: selection for translational accuracy." 2007 Mol. Biol. Evol. 24(2): 374-81.

* cited by examiner

*Primary Examiner* — Alana Harris Dent
*Assistant Examiner* — Anne Holleran
(74) *Attorney, Agent, or Firm* — Riverside Law LLP

(57) ABSTRACT

The invention provides compositions and methods for enhanced gene expression. The invention provides a composition comprising a 28-codon leader sequence operably linked to a desired gene which encodes the desired protein.

7 Claims, 12 Drawing Sheets

US 8,679,790 B2

LEADER SEQUENCE TO BOOST GENE EXPRESSION

BACKGROUND OF THE INVENTION

Recombinant DNA technology and genetic engineering has allowed for the introduction of foreign DNA sequences into cells for the expression of proteins of interest. However, obtaining high expression remains a challenge. Expression of important transgenes in a cell at high levels requires the ability to control the regulatory mechanisms governing expression. This requires suitable regulatory sequences that can function with the desired transgenes.

Production of recombinant proteins has been one of the major challenges within the biotechnological industry. Bacterial cells, in particular *Escherichia coli*, have been widely used as host cells for the production of recombinant polypeptides.

Polynucleotide compositions that provide enhanced gene expression provide certain benefits. These benefits include not only improved efficiency, cost-effectiveness, consistency and accuracy in improving the expression of certain genes, but also the ability to achieve a far greater scope of applicability. Current methods of enhancing gene expression include mutating regulator regions to increase transcription. In addition, mutation within the coding sequence can enhance protein stability. However, it would be desirable to have an approach to attain enhanced gene expression without having to alter a substantial number of codons of the gene or identify inhibitory sequences of the gene and then altering those sequences. The present invention provides a solution for the need in the art for enhancing gene expression.

SUMMARY OF THE INVENTION

The present invention provides a method of improving the expression efficiency of a desired gene. In one embodiment, the method comprises enhancing the expression of a desired protein in a cell by placing a leader sequence to the 5' terminus of a desired gene. In one embodiment, the leader sequence is place before the natural ATG translation codon for the desired gene. In another embodiment, the leader sequence is place after the natural ATG translation codon for the desired gene.

In one embodiment, the leader sequence comprises the nucleic acid sequence of SEQ ID NO: 12.

The present invention provides an isolated nucleic acid molecule comprising SEQ ID NO: 12.

In one embodiment, the nucleic acid molecule comprising SEQ ID NO: 12 is operably linked to a coding sequence. Preferably, the coding sequence is preceded by SEQ ID NO: 12.

The present invention provides an expression cassette for expressing a gene in a cell, wherein the cassette comprises operably linked elements comprising a promoter, a leader sequence, and a coding sequence, wherein the leader sequence comprises SEQ ID NO: 12.

The invention provides a cell comprising an expression cassette, wherein the cassette comprises operably linked elements comprising a promoter, a leader sequence, and a coding sequence, wherein the leader sequence comprises SEQ ID NO: 12.

The invention provides a method for enhancing expression of a gene in a cell. The method comprises expressing an expression cassette in a cell, wherein the cassette comprises operably linked elements comprising a promoter, a leader sequence, and a coding sequence, wherein the leader sequence comprises SEQ ID NO: 12.

The invention provides a kit for enhancing expression of a gene in a cell. The kit comprises an isolated nucleic acid molecule comprising SEQ ID NO: 12, the kit further comprising an instructional material for the use thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 1A through 1D, is a series of images depicting synthetic library of GFP genes with randomized codon usage. FIG. 1A demonstrates that degenerate oligonucleotides were mixed and assembled by polymerase chain reaction. Fragments were then cloned, sequenced, and assembled into complete GFP genes. Red indicates third-codon positions. Degenerate symbols are as follows: D (A or G or T); H (A or C or T); N (A or C or G or T); R (A or G); and Y (C or T). FIG. 1B depicts an example alignment illustrating sequence diversity among 15 synthetic genes. Shaded boxes indicate first and second codon positions, which are conserved across the library. FIGS. 1C and 1D depict the distribution of GC3 and CAI among the 154 synthetic GFP genes (1C) is representative of the diversity among the 4288 endogenous *E. coli* genes (1D).

FIGS. 2A through 2C, is a series of images depicting the determinants of gene expression. FIG. 2A demonstrates that codon adaptation was not significantly correlated with fluorescence among the 154 GFP constructs ($r=0.14$, $P=0.09$). FIG. 2B demonstrates that the predicted 5' mRNA folding energy was strongly correlated with fluorescence ($r=0.66$, $P<10^{-15}$). For each construct, folding energy was calculated in a window spanning positions $-4$ to $+37$ relative to translation start; two sample structures are shown. FIG. 2C depicts the sliding window analysis of mRNA folding and fluorescence. Local mRNA folding energies were calculated in a sliding window of length 42 nt. The significance of the correlation between local folding energy and fluorescence (negative $\log_{10} P$ value) is plotted as a function of window position along the sequence. Note the overlapping locations of the 30-nt ribosome-binding site (blue bar) and the window of strongest correlation between folding energy and fluorescence (partially overlapping red bar, nt $-4$ through nt $+37$).

FIG. 4 depicts an un-rooted tree generated by neighbor-joining, based on the pairwise hamming distances among 168 synthetic GFP genes.

FIGS. 6A and 6B, is a series of images depicting reproducibility of fluorescence measurements in standard experimental conditions. FIG. 6A depicts pGK8-GFP constructs induced with 1 mM IPTG and grown for 3 h at 37° C. Twenty four different pGK8-GFP constructs were grown in a 96-well plate, each in 4 replicates. Groups of neighboring bars of same color represent independent replicate clones with the same GFP sequence. FIG. 6B depicts average fluorescence of a set of 12 pGK8-GFP constructs, including two non-fluorescent mutants (bars 11 and 12). Error bars represent one standard error, n=14 to 18 experiments.

FIGS. 7A through 7D, is a series of images depicting reproducibility of fluorescence measurements across experimental conditions. FIG. 7A depicts fluorescence 3 h after induction (diamonds) or 6 h after induction (triangles) as a function of fluorescence 1.5 h after induction. pGK8-GFP clones were induced with 1 mM IPTG and grown at 37° C. FIG. 7B depicts Fluorescence in M9 (minimal) medium and LB (rich) medium. pGK8-GFP clones were induced with 1 mM IPTG and grown for 3 h at 37° C. FIG. 7C depicts fluorescence from T7 promoter (pGK8) and bacterial promoter (pGK14). pGK14-GFP constructs were transformed into DH5a cells, induced with 2% L-Arabinose and grown for 3 h at 37° C., while pGK8-GFP constructs were transformed into BL21-DE3 cells, induced with 1 mM IPTG and grown for 3 h at 37° C. FIG. 7D depicts fluorescence as a function of inducer concentration. pGK8-GFP constructs were induced with 1 mM or 0.02 mM IPTG and grown for 3 h at 37° C.

FIGS. 8A through 8C, is a series of images depicting Western and FACS measurements. FIG. 8A depicts the correlation between GFP fluorescence measured by FACS and by spectrofluorometer. FIG. 8B depicts a Western blot analysis of GFP protein levels. FIG. 8C depicts the correlation between GFP protein levels and fluorescence. Protein levels were assessed from the western blot analysis shown in FIG. 8B. pGK8-GFP constructs were used.

DETAILED DESCRIPTION OF THE INVENTION

Figure 1:
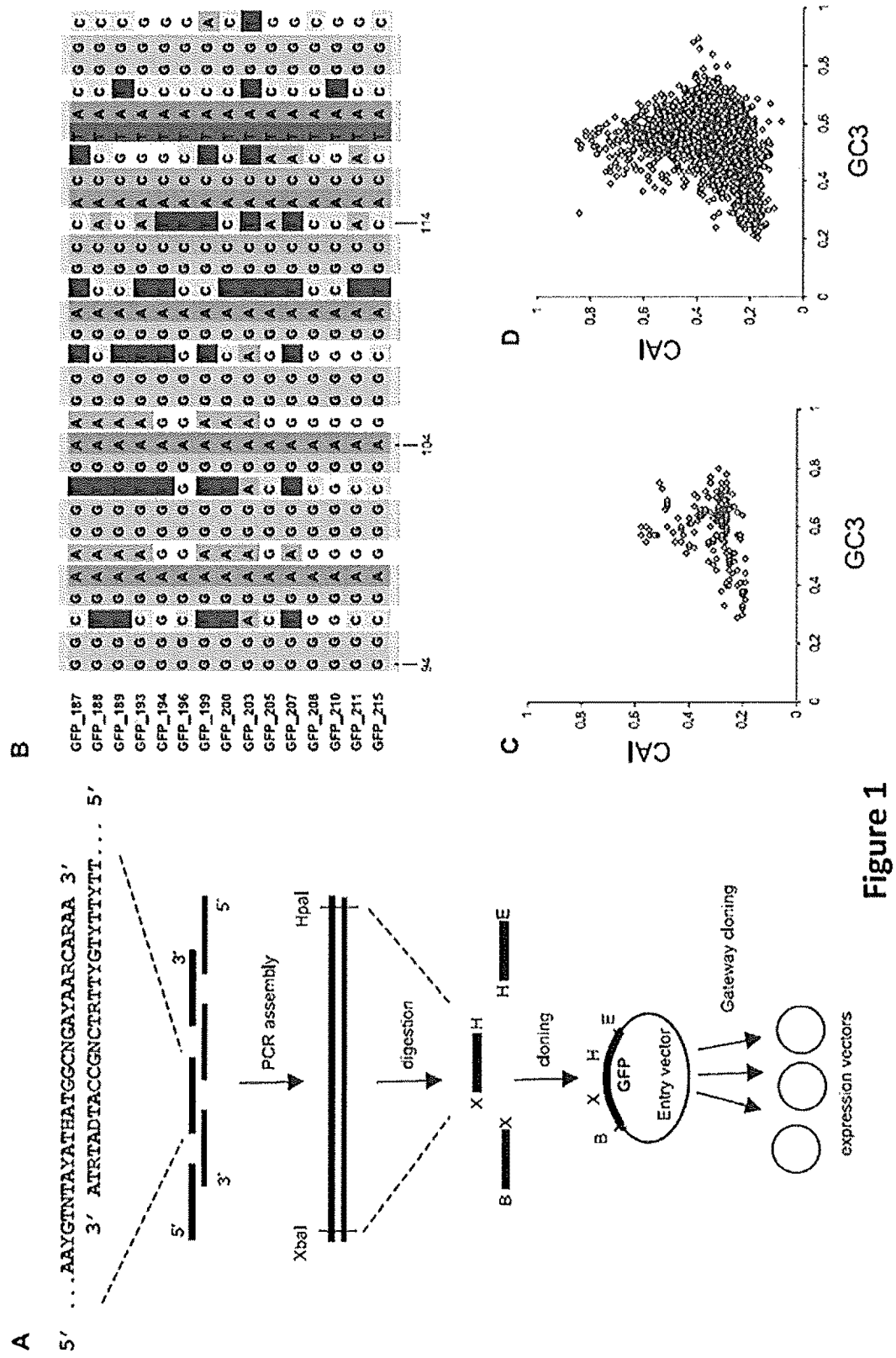
FIG. 1, comprising

The efficiency of a gene in expressing its protein product is a controlling factor in the attainment of appropriate levels of the protein in cells. The present invention is directed to improving the expression efficiency of such genes. Accordingly, the present invention encompasses methods and compositions for enhancing the expression of a desired protein in a cell by placing a leader sequence to the 5' terminus of a desired gene. In one embodiment, the leader sequence is place before the natural ATG translation codon for the desired gene. In another embodiment, the leader sequence is place after the natural ATG translation codon for the desired gene.

The present invention is based on the discovery that stability of mRNA folding near the ribosomal binding site contributes to controlling protein levels. It was observed that mRNA folding and associated rates of translation initiation play a predominant role in shaping expression levels of individual genes.

The present invention provides a method for the preparation of a protein, which method comprises culturing under such conditions that the protein is obtained from a cell comprising the leader sequence of the invention operably linked to a desired gene which encodes the desired protein, wherein the desired gene is preceded by the leader sequence: ATGGAATTATCACAAGTTTGTACAAAAAAGCAG-GCTGGCGCCGGAACC AATTCAGTCGACTGGATC-CAAGAAGGAGATATAACC (SEQ ID NO: 12), otherwise referred to as the 28-codon tag. Preferably, the leader sequence set forth in SEQ ID NO: 12 is translated.

The invention provides an expression cassette that is useful for improving expression of a desired gene in a cell. The cassette comprises the following elements that are operably linked from 5' to 3': 1) the 28-codon tag and 2) a coding sequence of interest. In one embodiment, the expression cassette comprises the following operably linked elements: a promoter, a leader sequence comprising SEQ ID NO: 12, and a coding sequence of interest.

The expression cassette is applicable to any situation where it is desirable to improve expression of a desired coding sequence. In some instances, the expression cassette is useful for improving expression over their wild-type counterparts or otherwise a coding sequence that is not operably linked to SEQ ID NO: 12. According, the present invention provides a method for enhancing expression of a gene comprising: expressing in vivo or in vitro a coding sequence of interest operably linked to SEQ ID NO: 12.

DEFINITIONS

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"Allogeneic" refers to a cell or biological compound derived from a different animal of the same species.

As used herein, the term "autologous" is meant to refer to any material derived from the same mammal to which it is later to be re-introduced into the mammal.

By the term "applicator," as the term is used herein, is meant any device including, but not limited to, a hypodermic syringe, a pipette, and the like, for administering the compounds and compositions of the invention.

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

By the term "effective amount", as used herein, is meant an amount that when administered to a mammal, causes a detectable level of mRNA and/or protein compared to the level of mRNA and/or protein detected in the absence of the compound. mRNA and/or protein level can be readily assessed by a plethora of art-recognized methods.

"Instructional material," as that term is used herein, includes a publication, a recording, a diagram, or any other medium of expression which can be used to communicate the usefulness of the composition and/or compound of the invention in the kit for effecting alleviating or treating the various diseases or disorders recited herein. Optionally, or alternately, the instructional material may describe one or more methods of alleviating the diseases or disorders in a cell or a tissue or a mammal, including as disclosed elsewhere herein.

The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., retroviruses, lentiviruses, adenoviruses, and adeno-associated viruses) that incorporate the recombinant polynucleotide.

A first region of an oligonucleotide "flanks" a second region of the oligonucleotide if the two regions are adjacent one another or if the two regions are separated by no more than about 1000 nucleotide residues, and preferably no more than about 100 nucleotide residues.

As used herein, the term "fragment" as applied to a nucleic acid, may ordinarily be at least about 18 nucleotides in length, preferably, at least about 24 nucleotides, more typically, from about 24 to about 50 nucleotides, preferably, at least about 50 to about 100 nucleotides, even more preferably, at least about 100 nucleotides to about 200 nucleotides, yet even more preferably, at least about 200 to about 300, even more preferably, at least about 300 nucleotides to about 400 nucleotides, yet even more preferably, at least about 400 to about 500, and most preferably, the nucleic acid fragment will be greater than about 500 nucleotides in length.

As applied to a protein, a "fragment" of a stimulatory or costimulatory ligand protein or an antigen, is about 6 amino acids in length. More preferably, the fragment of a protein is about 8 amino acids, even more preferably, at least about 10, yet more preferably, at least about 15, even more preferably, at least about 20, yet more preferably, at least about 30, even more preferably, about 40, and more preferably, at least about 50, more preferably, at least about 60, yet more preferably, at least about 70, even more preferably, at least about 80, and more preferably, at least about 100 amino acids in length amino acids in length.

A "genomic DNA" is a DNA strand which has a nucleotide sequence homologous with a gene as it exists in the natural host. By way of example, a fragment of a chromosome is a genomic DNA.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are completely or 100% homologous at that position. The percent homology between two sequences is a direct function of the number of matching or homologous positions, e.g., if half (e.g., five positions in a polymer ten subunits in length) of the positions in two compound sequences are homologous then the two sequences are 50% identical, if 90% of the positions, e.g., 9 of 10, are matched or homologous, the two sequences share 90% homology. By way of example, the DNA sequences 5'ATTGCC3' and 5'TATGGC3' share 50% homology.

In addition, when the terms "homology" or "identity" are used herein to refer to the nucleic acids and proteins, it should be construed to be applied to homology or identity at both the nucleic acid and the amino acid sequence levels.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence. In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

Preferably, when the nucleic acid encoding the desired protein further comprises a promoter/regulatory sequence, the promoter/regulatory is positioned at the 5' end of the desired protein coding sequence such that it drives expression of the desired protein in a cell. Together, the nucleic acid encoding the desired protein and its promoter/regulatory sequence comprise a "transgene."

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "polyadenylation sequence" is a polynucleotide sequence which directs the addition of a poly A tail onto a transcribed messenger RNA sequence.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, the term "transgene" means an exogenous nucleic acid sequence which exogenous nucleic acid is encoded by a transgenic cell or mammal.

A "recombinant cell" is a cell that comprises a transgene. Such a cell may be a eukaryotic cell or a prokaryotic cell.

By the term "exogenous nucleic acid" is meant that the nucleic acid has been introduced into a cell or an animal using technology which has been developed for the purpose of facilitating the introduction of a nucleic acid into a cell or an animal.

As used herein, to "treat" means reducing the frequency with which symptoms of a disease (i.e., viral infection, tumor growth and/or metastasis, or other effect mediated by decreased numbers and/or decreased activity of T cells, and the like) are experienced by a patient.

By the term "vector" as used herein, is meant any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of a nucleic acid that encodes a protein and/or antibody of the invention, to the patient, or to the aAPC, or the vector may be a non-viral vector which is suitable for the same purpose.

Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a lentiviral vector, a recombinant adenovirus, a recombinant retrovirus, a recombinant adeno-associated virus, a recombinant avian pox virus, and the like (Cranage et al., 1986, EMBO J. 5:3057-3063; International Patent Application No. WO 94/17810, published Aug. 18, 1994; International Patent Application No. WO 94/23744, published Oct. 27, 1994). Examples of non-viral vectors include, but are not limited to, liposomes, polyamine derivatives of DNA, and the like.

A "therapeutic" treatment is a treatment administered to a patient who exhibits signs of pathology for the purpose of diminishing or eliminating those signs and/or decreasing or diminishing the frequency, duration and intensity of the signs.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

To "treat" a disease as the term is used herein, means to reduce the frequency of the disease or disorder reducing the frequency with which a symptom of the one or more symptoms disease or disorder is experienced by an animal.

By the term "vaccine" as used herein, is meant a composition, a protein or a nucleic acid encoding a protein, or a cell, or the like which serves to protect an animal against a disease and/or to treat an animal already afflicted with a disease by inducing an immune response, compared with an otherwise identical animal to which the vaccine is not administered or compared with the animal prior to the administration of the vaccine.

As used herein, a "tumor antigen" means a protein, a polypeptide, or a peptide, which constitutes part of the tumor cell and is capable of inducing tumor-specific cytotoxic T lymphocytes. A tumor antigen peptide can be a peptide that is generated as a result of degradation of the tumor antigen in a tumor cell and can induce or activate tumor-specific cytotoxic T lymphocytes upon being expressed on the cell surface by binding to an HLA molecule (e.g., HLA-A*02). In addition, the site of the amino acid sequence which is capable of inducing tumor-specific cytotoxic T lymphocytes that is present in a tumor antigen is referred to a tumor antigen epitope (tumor antigen determinant).

DESCRIPTION

The present invention provides methods and compositions for enhancing gene expression. The present invention is based on the discovery that stability of mRNA folding near the ribosomal binding site contributes to variation in protein levels. It was observed that synonymous mutations did not alter the encoded protein, but rather influenced gene expression. Based on the disclosure presented herein, mRNA folding and associated rates of translation initiation play a predominant role in shaping expression levels of individual genes.

The present invention relates to polynucleotide compositions that provide enhanced efficiency in the expression of proteins or polypeptides by genes in a cell (i.e., resulting in an increase in the levels of the proteins or polypeptides encoded by the genes), as well as methods for preparing the compositions. In particular, the invention provides polynucleotide sequences that provide enhanced gene expression over the corresponding wild-type polynucleotides. The ability to enhance gene expression is applicable to any setting in which it is desirable to express a gene.

The present invention contemplates embodiments directed to any gene that is poorly expressed or any gene for which improved levels of protein expression is desirable for in vivo and/or in vitro uses.

Compositions

The present invention provides isolated nucleic acid molecules (polynucleotide molecules) comprising nucleotide base sequences that enhance expression of recombinant proteins. Such nucleic acid molecules are referred to herein as 28-codon tag (SEQ ID NO: 12). The presence of the 28-codon tag on an expression vector enhances the level of expression of one or more recombinant proteins encoded by one or more functional genes that reside on the expression vector as compared to the level of expression in the absence of the 28-codon tag. Such mediated enhancement of the level of expression of a recombinant protein is possible whether the 28-codon tag is located 5' to, 3' to (e.g., flanking) a gene encoding a recombinant protein(s) of interest. The 28-codon tag of the invention on an expression vector may enhance expression of one or more recombinant proteins whether encoded on separate corresponding genes or encoded on a single polycistronic gene present on the expression vector. The 28-codon tag may be used to enhance the level of expression of a recombinant protein using both stable expression systems and transient expression systems.

Typically, the 28-codon tag or otherwise referred to as a leader sequence is fused to the translation initiation codon of the desired gene it is wished to express. In such circumstances, therefore, the 5' end of the leader sequence is fused directly after the ATG translation start codon of the desired gene.

The 28-codon tag nucleic acid molecule comprising one or more of the nucleotide base sequences described herein may have any of a variety of forms including, without limitation, a linear nucleic acid molecule, a plasmid, a eukaryotic viral molecule, a prokaryotic viral (bacteriophage) molecule, an artificial chromosome, and a recombinant chromosome.

In a preferred embodiment, the invention provides an expression vector comprising at least the 28-codon tag described herein. Such a 28-codon tag-containing expression vector provides enhanced (elevated) levels of expression in an appropriate host cell of at least one recombinant protein encoded on the expression vector compared to the level of expression in the host cell carrying the same expression vector lacking the 28-codon tag. Expression vectors useful in the invention include any nucleic acid vector molecule that can be engineered to encode and express one or more recombinant proteins in an appropriate (homologous) host cell. Such expression vectors include, without limitation, eukaryotic plasmid vectors, eukaryotic viral vectors, prokaryotic plasmids, bacteriophage vectors, plant vectors, shuttle vectors (e.g., a vector that can replicate in eukaryotic and prokaryotic cells), mini-chromosomes, and various artificial chromosomes. Preferably, an expression vector is a plasmid expression vector, more preferably, a plasmid expression vector that stably integrates into a eukaryotic host cell genome, and even more preferably, a plasmid expression vector that stably integrates into a host cell genome by non-homologous recombination.

In another embodiment, the invention provides a host cell that contains an expression vector comprising the 28-codon tag described herein and a recombinant gene that directs the expression of at least one recombinant protein in the host cell. A host cell may be a eukaryotic or prokaryotic host cell. Preferred eukaryotic host cells for use in the invention include, without limitation, mammalian host cells, plant host cells, fungal host cells, eukaryotic algal host cells, protozoan host cells, insect host cells, and fish host cells. More preferably, a host cell useful in the invention is a mammalian host cell, including, but not limited to, a Chinese hamster ovary (CHO) cell, a COS cell, a Vero cell, an SP2/0 cell, an NS/0 myeloma cell, a human embryonic kidney (HEK 293) cell, a baby hamster kidney (BHK) cell, a HeLa cell, a human B cell, a CV-1/EBNA cell, an L cell, a 3T3 cell, a HEPG2 cell, a PerC6 cell, and an MDCK cell. Particularly preferred is a CHO cell that can be treated with a standard methotrexate treatment protocol to amplify the copy number of recombinant genes on an expression vector inserted into the host cell. Fungal cells that may serve as host cells in the invention include, without limitation, Ascomycete cells, such as *Aspergillus, Neurospora*, and yeast cells, particularly yeast of a genus selected from the group consisting of *Saccharomyces, Pichia, Hansenula, Schizosaccharomyces, Kluyveromyces, Yarrowia*, and *Candida*. Preferred yeast species that may serve as host cells for expression of recombinant proteins according to the invention include, but are not limited to, *Saccharomyces cerevisiae, Hansenula polymorpha, Kluyveromyces lactis, Pichia pastoris, Schizosaccharomyces pombe*, and *Yarrowia lipolytica*. Prokaryotic host cells that may be used for expressing recombinant proteins according to the invention include, without limitation, *Escherichia coli*, serovars of *Salmonella enterica, Shigella* species, *Wollinella succinogenes, Proteus vulgaris, Proteus mirabilis, Edwardsiella tarda, Citrobacter freundii, Pasteurella* species, *Haemophilus* species, *Pseudomonas* species, *Bacillus* species, *Staphyloccocus* species, and *Streptococcus* species. Other cells that may be used as host cells for expression of recombinant proteins according to the invention include protozoan cells, such as the trypanosomatid host *Leishmania tarcntolae*, and cells of the nematode *Caenorhaditis elegans*.

Polynucleotides as described herein, vectors comprising one or more 28-codon tags described herein, and host cells comprising such vectors comprising one or more 28-codon tags as described herein may be used in a variety methods related to expression of recombinant proteins of interest.

In one embodiment, the invention provides a method of enhancing expression of a recombinant protein of interest in a host cell comprising the step of inserting into a host cell a recombinant expression vector that comprises the 28-codon tag described herein and a recombinant gene that encodes and directs the synthesis of the recombinant protein of interest in the host cell and culturing the host cell under conditions promoting expression of the recombinant protein.

A recombinant protein whose expression may be enhanced by one or more 28-codon tags described herein may be any protein (including peptides, polypeptides, and oligomeric proteins) for which a functional gene(s) can be engineered into a nucleic acid vector molecule for expression in an appropriate host cell. Such proteins include, without limitation, soluble proteins, membrane proteins, structural proteins (i.e., proteins that provide structure or support to cells, tissues, or organs), ribosomal proteins, enzymes, zymogens, antibody molecules, cell surface receptor proteins, transcription regulatory proteins, translation regulatory proteins, chromatin proteins (e.g., histones), hormones, cell cycle regulatory proteins, G proteins, neuroactive peptides, immunoregulatory proteins (e.g., interleukins, cytokines), blood component proteins, ion gate proteins, heat shock proteins, dihydrofolate reductase, an antibiotic resistance protein, functional fragments thereof, epitope-containing fragments thereof, and combinations thereof.

Nucleic acid molecules containing the 28-codon tag described herein or portion thereof may also be used in as nucleic acid probes for identifying the presence of 28-codon sequences in other nucleic acid molecules by nucleic acid hybridization or as a source of primers for use in various polymerase chain reaction (PCR) procedures, e.g., as may be employed for manipulating, identifying, producing, or amplifying the 28-codon tag sequences described herein.

Nucleotide base sequences described herein also serve to provide the complementary sequences thereof. DNA molecules and nucleotide base sequences described herein also provide the corresponding RNA molecules and base sequences, wherein thymine (T) is replaced by uracil (U), and nucleic acid sequences complementary thereto.

Expression Cassette

In other related aspects, the invention includes an expression cassette that is useful for improving expression of a desired gene in a cell. The cassette comprises the following elements that are operably linked from 5' to 3': 1) the 28-codon tag and 2) a coding sequence of interest. In some instances, the 28-codon tag is fused directly after the ATG translation start codon of the desired gene.

In any event, the expression cassette for improved expression of a desired gene is operably linked to a nucleic acid comprising a promoter/regulatory sequence such that the nucleic acid is preferably capable of directing expression of the protein encoded by the nucleic acid corresponding to the expression cassette.

A promoter sequence is said to be "operably linked" to a coding DNA sequence if the two are situated such that the promoter DNA sequence influences the transcription of the coding DNA sequence. For example, if the coding DNA sequence codes for the production of a protein, the promoter DNA sequence would be operably linked to the coding DNA sequence if the promoter DNA sequence affects the expression of the protein product from the coding DNA sequence. For example, in a DNA sequence comprising a promoter DNA sequence physically attached to a coding DNA sequence in the same chimeric construct, the two sequences are likely to be operably linked.

The DNA sequence associated with the regulatory or promoter DNA sequence may be heterologous or homologous, that is, the inserted genes may be from a different species than the recipient cell. In either case, the DNA sequences, vectors and cells of the present invention are useful for directing transcription of the associated DNA sequence so that the mRNA transcribed or the protein encoded by the associated DNA sequence is efficiently expressed.

Promoters are positioned 5' (upstream) to the genes that they control. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art and demonstrated herein with multiple copies of regulatory elements, some variation in this distance can occur.

Any expressible foreign coding sequence can be used in the constructions of the invention. A foreign coding is the sequence of a gene comprising a DNA segment encoding a protein, polypeptide, antisense RNA or ribozyme or a portion thereof. Notwithstanding the adjective "foreign" the term "foreign coding sequence" can refer to a coding sequence naturally found within the cell, but artificially introduced. Foreign coding sequence may also encode a protein not normally found in the plant cell into which the gene is introduced, in which case it may be referred to as a heterologous coding sequence.

The coding sequence may be derived in whole or in part from a bacterial genome or episome, eukaryotic genomic, mitochondrial or plastid DNA, cDNA, viral DNA, or chemically synthesized DNA. It is possible that a coding sequence may contain one or more modifications in coding region which may affect the biological activity or the chemical structure of the expression product, the rate of expression, or the manner of expression control. Such modifications include, but are not limited to, mutations, insertions, deletions, rearrangements and substitutions of one or more nucleotides. The coding sequence may constitute an uninterrupted coding sequence or it may include one or more introns, bounded by the appropriate functional splice junctions. The coding sequence may be a composite of segments derived from a plurality of sources, naturally occurring or synthetic. The structural gene may also encode a fusion protein, so long as the experimental manipulations maintain functionality in the joining of the coding sequences.

In preparing the constructs of this invention, the various DNA fragments may be manipulated, so as to provide for the DNA sequences in the proper orientation and, as appropriate, in the proper reading frame. Adapters or linkers may be employed for joining the DNA fragments or other manipulations may be involved to provide for convenient restriction sites, removal of superfluous DNA, removal of restriction sites, or the like.

For expression of the desired gene, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. No. 4,683,202, U.S. Pat. No. 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2001). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A promoter sequence exemplified in the experimental examples presented herein is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

Vectors

The invention also encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The expression cassette comprising the 28-codon tag and the desired polynucleotide can be cloned into a number of types of vectors. However, the present invention should not be construed to be limited to any particular vector. Instead, the present invention should be construed to encompass a wide plethora of vectors which are readily available and/or well-known in the art.

A vector is any genetic element capable of serving as a vehicle of genetic transfer, expression, or replication for a foreign polynucleotide in a host cell. For example, a vector may be an artificial chromosome or a plasmid, and may be capable of stable integration into a host cell genome, or it may exist as an independent genetic element (e.g., episome, plasmid). A vector may exist as a single polynucleotide or as two or more separate polynucleotides. Vectors may be single copy vectors or multicopy vectors when present in a host cell. Preferred vectors for use in the present invention are expression vector molecules in which one or more functional genes can be inserted into the vector molecule, in proper orientation and proximity to expression control elements resident in the expression vector molecule so as to direct expression of one or more proteins when the vector molecule resides in an appropriate (homologous) host cell.

For example, the polynucleotide of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors. In specific embodiments, the expression vector is selected from the group consisting of a plant, viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

Expression vectors may include, without limitation, eukaryotic plasmid vectors, eukaryotic viral vectors, prokaryotic plasmids, bacteriophage vectors, shuttle vectors (e.g., a vector that can replicate in eukaryotic and prokaryotic cells), mini-chromosomes, and various artificial chromosomes (e.g., bacterial artificial chromosomes (BACs), yeast artificial chromosomes (YACs)). Preferably, an expression vector used in the invention is a plasmid, more preferably, a plasmid expression vector that stably integrates into a host cell genome, and, even more preferably, a plasmid expression vector that stably integrates into a host cell genome by non-homologous recombination. A "shuttle vector" (or bi-functional vector) refers to any vector that can replicate in more than one species of organism. For example, a shuttle vector that can replicate in both *Escherichia coli* (*E. coli*) and *Saccharomyces cerevisiae* (*S. cerevisiae*) can be constructed by linking sequences from an *E. coli* plasmid with sequences from the yeast plasmid.

Expression systems comprise an expression vector and appropriate (homologous) host cell that will express the recombinant protein(s) encoded on the expression vector. An expression system may be a stable expression system or a transient expression system. In a stable expression system, an expression vector stably integrates into the host cell genome or is continuously replicated and faithfully passed on to both daughter cells so that host cells are able to continue to express the recombinant protein(s) when cultured under the appropriate conditions. In a transient expression system, expression vector molecules are not retained in both daughter cells and eventually are lost or so diminished in a growing cell culture that expression of recombinant protein(s) from the culture will eventually cease or be so low as to not be useful for most production purposes. Expression vectors used in the Examples, below, are types of shuttle vectors that can replicate to relatively high copy numbers when inserted (e.g., by transformation) into *E. coli* cells and that can also be inserted (e.g., by transfection) into and stably maintained in Chinese hamster ovary (CHO) cells to obtain stable expression of their encoded gene product(s) of interest (Kaufman et al., Molec. Cell, Biol., 5: 1750-1759 (1980)) or that can be transiently maintained in HEK 293 cells (Durocher et al., Nucleic Acids Res., 30: E9). Thus, the 28-codon tag described herein may be used to enhance expression of a recombinant protein(s) of interest in both stable and transient expression systems.

Exemplary eukaryotic vectors that may be used in the invention include, but are not limited to, viral and non-viral vectors. Viral vectors include, without limitation, retroviral vectors (including lentiviral vectors); adenoviral vectors including replication competent, replication deficient, and gutless forms thereof; adeno-associated virus (AAV) vectors; simian virus 40 (SV-40) vectors; bovine papilloma virus vectors; Epstein-Barr virus vectors; herpes virus vectors, vaccinia virus vectors; Maloney murine leukemia virus vectors; Harvey murine sarcoma virus vectors, murine mammary tumor virus vectors, and Rous sarcoma virus vectors, Baculovirus vectors are well known and are suitable for expression in insect cells.

A variety of vectors suitable for expression in eukaryotic or prokaryotic cells are well known in the art, and many are commercially available. Commercial sources include, without limitation, Stratagene (La Jolla, Calif.), Invitrogen (Carlsbad, Calif.), Promega (Madison, Wis.), and Sigma-Aldrich (St. Louis, Mo.). Many vector sequences are available through GenBank, and additional information concerning vectors is available on the internet via the Riken BioSource Center.

In order to assess the expression of the desired gene, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479: 79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Host Cells for Enhanced Production of Polypeptides of Interest

A polynucleotide that contains a coding sequence for one or more proteins that is operably linked to a promoter sequence and possibly other transcriptional regulatory sequences to direct proper transcription of the coding sequence into messenger RNA (mRNA) and that also comprises any of a variety of translation regulatory sequences that may be necessary or desired to direct proper translation of the mRNA into the desired protein in the intended host cell. A translational start codon (e.g., ATG) and a ribosome binding site are typically required in the mRNA for translation to occur in prokaryotic and eukaryotic cells. Other translation regulatory sequences that may also be employed, depending on the host cell, include, but are not limited to, an RNA splice site and a polyadenylation site.

The 28-codon tag of the invention has an effect to the ribosomal binding site. Accordingly, the 28-codon tag is fused directly after the ATG translation start codon of the desired gene. This serves to enhance the level of expression of one or more recombinant proteins encoded by one or more functional genes that reside on the expression vector as compared to the level of expression in the absence of the 28-codon tag in a host cell.

A host cell can be any cell, i.e., any eukaryotic or prokaryotic cell, into which a vector molecule can be inserted. According to the present invention, preferred host cells are eukaryotic or prokaryotic cells, including, but not limited to, animal cells (e.g., mammalian, bird, and fish host cells), plant cells (including eukaryotic algal cells), fungal cells, bacterial cells, and protozoan cells. Host cells useful in the invention may be of any genetic construct, but are preferably haploid or diploid cells. Preferred mammalian host cells useful in the invention include, without limitation, a Chinese hamster ovary (CHO) cell, a COS cell, a Vero cell, an SP2/0 cell, an NS/0 myeloma cell, a human embryonic kidney (HEK 293) cell, a baby hamster kidney (BHK) cell, a HeLa cell, a human B cell, a CV-1/EBNA cell, an L cell, a 3T3 cell, an HEPG2 cell, a PerC6 cell, and an MDCK cell. A preferred insect cell is Sf9. Fungal cells that may serve as host cells in the invention include, without limitation, Ascomycete cells, such as *Aspergillus, Neurospora*, and yeast cells, particularly yeast of the genera *Saccharomyces, Pichia, Hansenula, Schizosaccharomyces, Kluyveromyces, Yarrowia*, and *Candida*. Particularly preferred yeast fungal species that may serve as host cells for expression of recombinant proteins are *Saccharomyces cerevisiae, Hansenula polymorpha, Kluyveromyces lactis, Pichia pastoris, Schizosaccharomyces pombe*, and *Yarrowia lipolytica*. Preferred prokaryotic cells that may serve as host cells in the invention include, without limitation, *Escherichia coli*, serovars of *Salmonella enterica, Shigella* species, *Wollinella succinogenes, Proteus vulgaris, Proteus mirabilis, Edwardsiella tarda, Citrobacter freundii, Pasteurella* species, *Haemophilus* species, *Pseudomonas* species, *Bacillus* species, *Staphyloccocus* species, and *Streptococcus* species. Other cells that may be useful host cells for the expression of recombinant proteins according to the invention include protozoans, such as the trypanosomatid host *Leishmania tarentolae*, and cells of the nematode *Caenorhaditis elegans*. Various expression vectors are available for use in the aforementioned cells.

There are a variety of means and protocols for inserting vector molecules into cells including, but not limited to, transformation, transfection, cell or protoplast fusion, use of a chemical treatment (e.g., polyethylene glycol treatment of protoplasts, calcium treatment, transfecting agents such as LIPOFECTIN™ and LIPOFECTAMINE™ transfection reagents available from Invitrogen (Carlsbad, Calif.), use of various types of liposomes, use of a mechanical device (e.g., nucleic acid coated microbeads), use of electrical charge (e.g., electroporation), and combinations thereof. It is within the skill of a practitioner in the art to determine the particular protocol and/or means to use to insert a particular vector molecule described herein into a desired host cell.

Methods for transferring nucleic acid sequence information from one vector or other nucleic acid molecule to another are not limiting in the present invention and include any of a variety of genetic engineering or recombinant nucleic acid techniques known in the art. Particularly preferred transfer techniques include, but are not limited to, restriction digestion and ligation techniques, polymerase chain reaction (PCR) protocols (utilizing specific or random sequence primers), homologous recombination techniques (utilizing polynucleotide regions of homology), and non-homologous recombination (e.g., random insertion) techniques. Nucleic acid molecules containing a specific sequence may also be synthesized, e.g., using an automated nucleic acid synthesizer, and the resulting nucleic acid product then incorporated into another nucleic acid molecule by any of the aforementioned methodologies.

Employing genetic engineering technology necessarily requires growing recombinant host cells (e.g., transfectants, transformants) under a variety of specified conditions as determined by the requirements of the cells and the particular cellular state desired by the practitioner. For example, a host cell may possess (as determined by its genetic disposition) certain nutritional requirements, or a particular resistance or sensitivity to physical (e.g., temperature) and/or chemical (e.g., antibiotic) conditions. In addition, specific culture conditions may be necessary to regulate the expression of a desired gene (e.g., the use of inducible promoters), or to initiate a particular cell state (e.g., yeast cell mating or sporulation). These varied conditions and the requirements to satisfy such conditions are understood and appreciated by practitioners in the art.

The recombinant vectors harboring the gene of interest and the 28-codon tag described herein can be introduced into an appropriate host cell by any means known in the art. For example, the vector can be transfected into the host cell by calcium phosphate co-precipitation, by conventional mechanical procedures such as microinjection or electroporation, by insertion of a plasmid encased in liposomes, and by virus vectors. These techniques are all well known and routinely practiced in the art, e.g., Brent et al., Current Protocols in Molecular Biology, John Wiley & Sons, Inc. (ringbou ed., 2003); and Weissbach & Weissbach, Methods for Plant Molecular Biology, Academic Press, NY, Section VIII, pp. 42 1-463, 1988. Host cells which harbor the transfected recombinant vector can be identified and isolated using the selection marker present on the vector. Large numbers of recipient cells may then be grown in a medium which selects for vector-containing cells. These cells may be used directly or the expressed recombinant protein may be purified in accordance with conventional methods such as extraction, precipitation, chromatography, affinity methods, electrophoresis and the like. The exact procedure used will depend upon the specific protein produced and the specific vector/host expression system utilized.

In an embodiment, host cells for expressing the recombinant vectors are eukaryotic cells. Eukaryotic vector/host systems, and mammalian expression systems, allow for proper post-translational modifications of expressed mammalian proteins to occur, e.g., proper processing of the primary transcript, glycosylation, phosphorylation and advantageously secretion of expressed product. Therefore, eukaryotic cells such as mammalian cells can be the host cells for the protein of a polypeptide of interest. Examples of such host cell lines include CHO, BHK, HEK293, VERO, HeLa, COS, MDCK, NS0 and W138.

In some embodiments, engineered mammalian cell systems that utilize recombinant viruses or viral elements to direct expression of the protein of interest are employed. For example, when using adenovirus expression vectors, the coding sequence of a protein of interest along with the 28-codon tag may be ligated to an adenovirus transcription/translation control complex, e.g., the late promoter and tripartite leader sequence. This chimeric gene may then be inserted into the adenovirus genome by in vitro or in vivo recombination. Insertion in a non-essential region of the viral genome (e.g., region E1 or E3) will result in a recombinant virus that is viable and capable of expressing the polypeptide of interest in infected hosts (e.g., see Logan & Shenk, Proc. Natl. Acad. Sci. USA 81:3655-3659, 1984). Alternatively, the vaccinia virus 7.5K promoter may be used. (e.g., see, Mackett et al., Proc. Natl. Acad. Sci. USA, 79:7415-7419, 1982; Mackett et al., J. Virol, 49:857-864, 1984; Panicali et al., Proc. Natl. Acad, Sci, USA, 79:4927-4931, 1982). Of particular interest are vectors based on bovine papilloma virus which have the ability to replicate as extrachromasomal elements (Sarver et al., Mol. Cell. Biol. 1:486, 1981), These vectors can be used for stable expression by including a selectable marker in the plasmid, such as the neo gene. Alternatively, the retroviral genome can be modified for use as a vector capable of introducing and directing the expression of the gene of interest in host cells (Cone & Mulligan, Proc, Natl. Acad. Sci. USA 8 1:6349-6353, 1984). High level expression may also be achieved using inducible promoters, including, but not limited to, the metallothionine IIA promoter and heat shock promoters.

The host cell for expression of the recombinant vectors can also be yeast. In yeast, a number of vectors containing constitutive or inducible promoters may be used. See, e.g., Brent et al., Current Protocols in Molecular Biology, John Wiley & Sons, Inc. (ringbou ed., 2003); and The Molecular Biology of the Yeast *Saccharomyces*, Strathem et al. (eds.), Cold Spring Harbor Press (1982). A constitutive yeast promoter such as ADH or LEU2 or an inducible promoter such as GAL may be used. Alternatively, vectors may be used which promote integration of foreign DNA sequences into the yeast chromosome.

In cases where plant expression vectors are used, the expression of a gene of interest may be driven by any of a number of promoters. For example, viral promoters such as the .sup.35S RNA and 19S RNA promoters of CaMV (Brisson et al., Nature 310.about.511-514, 1984) or the coat protein promoter to TMV (Takamatsu et al., EMBO J., 6:307-3 11, 1987) may be used. Alternatively, plant promoters such as the small subunit of RUBISCO (Coruzzi et al., EMBO J. 3:16711680, 1984; and Broglie et al., Science 224:838-843, 1984) or heat shock promoters (Gurley et al., Mol. Cell. Biol., 6:559-565, 1986) may be used.

Once the recombinant vector has been introduced into the appropriate host cells, the expressed recombinant protein may be purified in accordance with conventional methods such as extraction, precipitation, chromatography, affinity chromatography, electrophoresis and the like. The exact procedure used will depend upon both the specific protein produced and the specific expression system utilized. For long-term, high-yield production of recombinant proteins, stable expression is preferred. Rather than using expression vectors which contain origins of replication, host cells can be transformed with a vector that allows stable integration of the vector into the host chromosomes. Host cells with stably integrated polynucleotides that encode the protein of interest can grow to form foci which in turn can be cloned and expanded into cell lines. For example, following the introduction of foreign DNA, engineered cells may be allowed to grow for 1-2 days in an enriched media, and then switched to a selective media.

Therapeutic Applications

An appropriate level of a protein in mammalian cells is a critical factor for inducing an immunological and/or therapeutic response, e.g., the use of the gene and its protein product as an immunogen, DNA vaccine, co-immunogen, adjuvant, carrier protein or vector, therapeutic agent, diagnostic agent, therapeutic, immuno-prophylactic, immuno-therapeutic, etc., The efficiency of a gene in expressing its protein product is a controlling factor in the attainment of appropriate levels of the protein in cells. Certain genes fail to provide appropriate protein levels in mammalian cells. The present invention is directed to improving the expression efficiency of such genes.

A vector for therapeutic expression of proteins can be constructed with the 28-codon tag described elsewhere herein and a polynucleotide encoding a therapeutic protein. Other examples include vectors to be used in vaccines so that increased antigen production can be achieved.

In some embodiments, the translational enhancer elements and polynucleotides disclosed herein are used in the preparation of DNA vaccines. In order to produce increased antigen levels, the DNA vaccines can be generally comprised of an expression vector wherein expression of a vaccine antigen is enhanced by the presence of one or more of the 28-codon tags. In some embodiments, the DNA vaccines can deliver and express more than one antigen. Other than sequences encoding the vaccine antigen and the translational enhancer elements, the DNA vaccine vector typically also includes a promoter for transcription initiation that is active in eukaryotic cells. Such DNA vaccine vectors can be generated in accordance with the methods well known in the art. For example, methods for making and using DNA vaccine for a given antigen are described in, e.g., Gurunathan et al., Ann. Rev. Immunol., 18:927, 2000; Krieg, Biochim. Biophys. Acta., 1489:107, 1999; Cichutek, Dev. Biol. Stand., 100:119, 1999; Davis, Microbes Infect., 1:7, 1999; and Leitner, Vaccine, 18:765, 1999.

Any of the vectors described above may be employed to express a vaccine antigen in the DNA vaccines. Additional vectors that can be used to construct DNA vaccines can include viral vectors such as ALVAC (a canarypox virus), MVA (a cowpox variant), and ADV5 (adenovirus 5) vectors, as well as plasmid vectors such as pUC19 (ATCC#37254), pcDNA3.1 (Invitrogen, Carlsbad, Calif.), pNGVL (National Gene Vector Laboratory, University of Michigan, Mich.), p414cyc (ATCC#87380), pBSL130 (ATCC#87145), and pECV25 (ATCC#77187). Examples of promoters that can be employed in the vaccine vectors include, e.g., the SV40 early promoter, the cytomegalovirus immediate early promoter/enhancer, and various eukaryotic promoters described herein.

A diverse array of vaccine antigens can be expressed by the DNA vaccines. These include, e.g., HIV-1 antigens, Hepatitis C virus antigens, Hepatitis B virus antigens, Herpes Simplex viral antigens, Pox virus antigens, Influenza virus antigens, Measles virus antigens, Dengue virus antigens, *Entamoeba histolytica* antigens, Semliki Forest virus antigens, Papilloma virus antigens, *Plasmodium vivax* and *Plasmodium falciparum* antigens. Additional information of antigens that can be expressed in the DNA vaccines are known in the art.

The DNA vaccines can be used to immunize any subject in need of prevention or protection against infection of a pathogen (e.g., HIV infection). Such subjects include humans and non-human animals such as rodents (e.g. mice, rats and guinea pigs), swine, chickens, ferrets, non-human primates. Methods of administering a DNA vaccine to a suitable subject are described in the art. See, e.g., Webster et al, Vacc., 12:1495-1498, 1994; Bernstein et al., Vaccine, 17:1964, 1999; Huang et al., Viral Immunol., 12:1, 1999; Tsukamoto et al., Virol. 257:352, 1999; Sakaguchi et al., Vaccine, 14:747, 1996; Kodihalli et al., J. Virol., 71: 3391, 1997; Donnelly et al., Vaccine, 15:865, 1997; Fuller et al., Vaccine, 15:924, 1997; Fuller et al., Immunol. Cell Biol., 75: 389, 1997; Le et al., Vaccine, 18:1893, 2000; Boyer et al., J. Infect. Dis., 181: 476, 2000.

In addition to enhancing expression of the vaccine antigens by using one or more of the 28-codon tags described herein, the DNA vaccines can also be formulated with an adjuvant. Suitable adjuvants that can be employed include, e.g., aluminum phosphate or aluminum hydroxyphosphate, monophosphoryl-lipid A, QS-21 saponin, dexamethasone, CpG DNA sequences, Cholera toxin, cytokines or chemokines. Such adjuvants enhance immunogenicity of the DNA vaccines. Methods of preparing such modified DNA vaccines are known in the art. See, e.g., Ulmer et al., Vaccine 18:18, 2000; Schneerson et al. J. Immunol. 147:2136-2140, 1991; Sasaki et al. Inf. Immunol. 65: 3520-3528, 1997; Lodmell et al. Vaccine 18:1059-1066, 2000; Sasali et al., J. Viral. 72:4931, 1998; Malone et al., J. Biol. Chem. 269:29903, 1994; Davis et al., J. Immunol. 15:870, 1998; Xin et al., Clin. Immunol., 92:90, 1999; Agren et al., Immunol. Cell Biol. 76:280, 1998; and Hayashi et al. Vaccine, 18: 3097-3105, 2000.

In some embodiments, provided are methods for enhancing expression of a therapeutic protein in the treatment of various diseases. In these methods, an expression vector harboring a translational enhancer element or polynucleotide and expressing a therapeutic protein are transfected into target cells, ex vivo or in vivo, through the interaction of the vector and the target cell. The compositions are administered to a subject in an amount sufficient to elicit a therapeutic response in the subject. Such gene therapy procedures have been used to correct acquired and inherited genetic defects, cancer, and viral infection in a number of contexts. See, e.g., Anderson, Science 256:808-813, 1992; Nabel & Felgner, TIBTECH 11:211-217, 1993; Mitani & Caskey, TIBTECH 11:162-166, 1993; Mulligan, Science 926-932, 1993; Dillon, TIBTECH 11: 167-175, 1993; Miller, Nature 357:455-460, 1992; Van Brunt, Biotechnology 6:1149-1154, 1998; Vigne et al., Restorative Neurol. and Neurosci. 8:35-36, 1995; Kremer & Perricaudet, Br. Med. Bull. 51:31-44, 1995; Haddada et al., in Current Topics in Microbiology and Immunology (Doerfler & Bohm eds., 1995); and Yu et al., Gene Therapy 1: 13-26, 1994.

Various diseases and disorders are suitable for treatment with the therapeutic methods described herein. These include malignancies of the various organ systems, e.g., lung, breast, lymphoid, gastrointestinal, and genito-urinary tract. Also suitable for treatment are adenocarcinomas which include malignancies such as most colon cancers, renal-cell carcinoma, prostate cancer, non-small cell carcinoma of the lung, cancer of the small intestine, and cancer of the esophagus. A recombinant expression vector containing the 28-codon tag disclosed herein is also useful in treating non-malignant cell-proliferative diseases such as psoriasis, pemphigus vulgaris, Behcet's syndrome, and lipid histiocytosis. Essentially, any disorder that can be treated or ameliorated with a therapeutic protein is considered susceptible to treatment with an expression vector that expresses the therapeutic protein at increased level due to the presence of the translational enhancer element in the vector.

A large number of delivery methods can be used to practice the therapeutic methods described herein. These methods are all well known to those of skill in the art. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. No. 5,049,386, U.S. Pat. No. 4,946,787; and U.S. Pat. No. 4,897,355 and lipofection reagents are sold commercially (e.g., Transfectam™ and Lipofectin™). Cationic and neutral lipids that are suitable for efficient receptor-recognition lipofection of polynucleotides include those described in, e.g., WO 91/17424 and WO 91/16024. Delivery can be to cells (ex vivo administration) or target tissues (in vivo administration).

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al. (Proc. Natl. Acad. Sci. USA. 92:9747-9751, 1995) reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

The expression vectors can be delivered in vivo by administration to an individual subject, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual subject (e.g., lymphocytes, bone marrow aspirates, tissue biopsy) or universal donor hematopoietic stem cells, followed by reimplantation of the cells into a subject, usually after selection for cells which have incorporated the vector. Ex vivo cell transfection for diagnostics, research, or for gene therapy (e.g., via re-infusion of the transfected cells into the host organism) is well known to those of skill in the art. In an embodiment, cells can be isolated from the subject organism, transfected with a nucleic acid (gene or cDNA), and re-infused back into the subject organism (e.g., subject). Various cell types suitable for ex vivo transfection are well known to those of skill in the art (see, e.g., Freshney et al., Culture of Animal Cells, A Manual of Basic Technique (3rd ed. 1994)) and the references cited therein for a discussion of how to isolate and culture cells from subjects).

Plant Application

The 28-codon tag of the invention can be used to enhance expression of proteins desirable in the context of growing plants. Examples, proteins known to inhibit insects or plant pathogens such as fungi, bacteria and nematodes. These proteins include, but are not limited to, plant non-specific lipid acyl hydrolases, especially patatin; midgut-effective plant cystatins, especially potato papain inhibitor; magainins, Zasloff (1987), PNAS USA, 84:5449 5453; cecropins, Hultmark et al. (1982), EUR. J. Biochem., 127:207 217; attacins, Hultmark et al. (1983), EMBO J., 2:571 576; melittin; gramicidin S, Katsu et al. (1988), Biochim. Biophys. Acta, 939:57 63; sodium channel proteins and synthetic fragments, Oiki et al. (1988), PNAS USA, 85:2393 2397: the alpha toxin of Staphylococcus aureus, Tobkes et al. (1985), Biochem. 24:1915 1920; apolipoproteins and fragments thereof; Knott et al. (1985), Science, 230:37; alamethicin and a variety of synthetic amphipathic peptides, Kaiser et al. (1987), Ann. Rev Biophys. Biophys. Chem., 16:561 581); lectins, L is et al. (1986), Atm. Rev. Biochem., 55:35 68 and Van Parijis et al. (1991), Planta, 183:258; pathogenesis-related proteins, Linthorst (1991), Critical Rev. Plant Sci., 10:123 150; osmotins and permatins, Vigers et al. (1992), Plant Sci., 83:155; chitinases; glucanases, Lewah et al. (1991), J. Biol. Chem., 266:1564 1573; thionins, Bohlmann and Apel (1991), Annu. Rev. Plant Physiol Plant Mol. Biol., 42:227 240; protease inhibitors, Ryan (1990), Annu Rev. Phvtopathol., 28:425; plant anti-microbial peptides, Cammue et al. (1992), J. Biol. Chem., 267:2228 2233; and polypeptides from *Bacillus thuringiensis*, which are postulated to generate small pores in the insect gut cell membrane, nowles et al. (1987), Biochim. Biophys. Acta 924:509 518 and Hofte and Whitely (1989), Microbiol. Rev., 53:242 255.

Vectors are available or can be readily prepared for transformation of plant cells. In general, plasmid or viral vectors should contain all the DNA control sequences necessary for both maintenance and expression of a heterologous DNA sequence in a given host. Such control sequences generally include a leader sequence and a DNA sequence coding for translation start-signal codon, a translation terminator codon, and a DNA sequence coding for a 3' UTR signal controlling messenger RNA processing. Selection of appropriate elements to optimize expression in any particular species is a matter of ordinary skill in the art utilizing the teachings of this disclosure; in some cases hybrid constructions are preferred, combining promoter elements upstream of the tissue preferential promoter TATA and CAAT box to a minimal 35S derived promoter consisting of the 35S TATA and CAAT box. Finally, the vectors should desirably have a marker gene that is capable of providing a phenotypical property which allows for identification of host cells containing the vector, and an intron in the 5' untranslated region, e.g., intron 1 from the maize alcohol dehydrogenase gene that enhances the steady state levels of mRNA of the marker gene.

The activity of the foreign coding sequence inserted into plant cells is dependent upon the influence of endogenous plant DNA adjacent the insert. Generally, the insertion of heterologous genes appears to be random using any transformation technique; however, technology currently exists for producing plants with site specific recombination of DNA into plant cells (see WO 91/09957). The particular methods used to transform such plant cells are not critical to this invention, nor are subsequent steps, such as regeneration of such plant cells, as necessary. Any method or combination of methods resulting in the expression of the desired sequence or sequences under the control of the promoter is acceptable.

There are many methods well know in the art for introducing transforming DNA segments into cells, but not all are suitable for delivering DNA to plant cells. Suitable methods are believed to include virtually any method by which DNA can be introduced into a cell, such as by *Agrobacterium* infection, direct delivery of DNA, for example, by PEG-mediated transformation of protoplasts (Omirulleh et al., Plant Molecular Biology, 21:415 428, 1993.), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introducing DNA into cells is well-known to those of skill in the art. Four basic methods for delivering foreign DNA into plant cells have been described, Chemical methods (Graham and van der Eb, Virology, 54(02):536 539, 1973; Zatloukal, Wagner, Cotten, Phillips, Plank, Steinlein, Curiel, Birnstiel, Ann. N.Y. Acad. Sci., 660:136 153, 1992); Physical methods including microinjection (Capecchi, Cell, 22(2):479 488, 1980), electroporation (Wang and Neumann, Biochim. Biophys. Res. Conmmun. 107(2):584 587, 1982; Fromm, Taylor, Walbot, Proc. Natl. Acad. Sci. USA, 82(17): 5824 5828, 1985; U.S. Pat. No. 5,384,253) and the gene gun (Johnston and Tang, Methods Cell. Biol., 43 (A):353 365, 1994; Fynan, Webster, Fuller, Haynes, Santoro, Robinson, Proc. Natl. Acad. Sci. USA 90(24):11478 11482, 1993); Viral methods (Clapp, Clin. Perinatol., 20(1):155 168, 1993; Lu, Xiao, Clapp, Li, Broxmeyer, J. Exp. Med. 178(6):2089 2096, 1993; Eglitis and Anderson, Biotechniques, 6(7):608 614, 1988; Eglitis, Kantoff, Kohn, Karson, Moen, Lothrop, Blaese, Anderson, Avd. Exp. Med. Biol., 241:19 27, 1988); and Receptor-mediated methods (Curiel, Agarwal, Wagner, Cotten, Proc. Natl. Acad. Sci. USA, 88(19):8850 8854, 1991; Curiel, Wagner, Cotten, Birnstiel, Agarwal, Li, Loechel, Hu, Hum, Gen. Ther., 3(2):147 154, 1992; Wagner et al., Proc. Natl. Acad. Sci. USA, 89 (13):6099 6103, 1992).

The introduction of DNA into plant cells by means of electroporation is well-known to those of skill in the art. Plant cell wall-degrading enzymes, such as pectin-degrading enzymes, are used to render the recipient cells more susceptible to transformation by electroporation than untreated cells. To effect transformation by electroporation one may employ either friable tissues such as a suspension culture of cells, or embryogenic callus, or immature embryos or other organized tissues directly. It is generally necessary to partially degrade the cell walls of the target plant material to pectin-degrading enzymes or mechanically wounding in a controlled manner. Such treated plant material is ready to receive foreign DNA by electroporation.

Another method for delivering foreign transforming DNA to plant cells is by microprojectile bombardment. In this method, microparticles are coated with foreign DNA and delivered into cells by a propelling force. Such micro particles are typically made of tungsten, gold, platinum, and similar metals. An advantage of microprojectile bombardment is that neither the isolation of protoplasts (Cristou et al., 1988, Plant Physiol., 87:671 674,) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen onto a filter surface covered with corn cells cultured in suspension. The screen disperses the particles so that they are not delivered to the recipient cells in large aggregates. For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids.

*Agrobacterium*-mediated transfer is a widely applicable system for introducing foreign DNA into plant cells because the DNA can be introduced into whole plant tissues, eliminating the need to regenerate an intact plant from a protoplast. The use of *Agrobacterium*-mediated plant integrating vectors to introduce DNA into plant cells is well known in the art. See, for example, the methods described in Fraley et al., 1985, Biotechnology, 3:629; Rogers et al., 1987, Meth. in Enzymol., 153:253 277. Further, the integration of the Ti-DNA is a relatively precise process resulting in few rearrangements. The region of DNA to be transferred is defined by the border sequences, and intervening DNA is usually inserted into the plant genome as described in Spielmann et al., 1986, Mol. Gen. Genet., 205:34; Jorgensen et al., 1987, Mol. Gen. Genet., 207:471.

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate construction of vectors capable of expressing various proteins or polypeptides. The vectors described (Rogers et al., 1987), have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations.

Transformation of plant protoplasts can be achieved using methods based on calcium phosphate precipitation, polyethylene glycol treatment, electroporation, and combinations of these treatments (see, e.g., Pottykus et al., 1985, Mol. Gen. Genet., 199:183; Marcotte et al., Nature, 335:454, 1988). Application of these systems to different plant species depends on the ability to regenerate the particular species from protoplasts.

EXAMPLE

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Coding-Sequence Determinants of Gene Expression in *Escherichia coli*

The following examples demonstrate that the stability of mRNA folding near the ribosomal binding site contributed to variation in protein levels. The results demonstrate that mRNA folding and associated rates of translation initiation play a predominant role in shaping expression levels of individual genes, whereas codon bias influences global translation efficiency and cellular fitness.

The materials and methods employed in the experiments disclosed herein are now described.
Gene Synthesis In order to synthesize a library of genes with randomized codon usage, the EGFP protein sequence (gi: 1543069) was reverse translated the into a degenerate nucleotide sequence. Four reverse-translation methods were used to obtain degenerate sequences with varying GC content bias and *E. coli* codon adaptation index. The degenerate nucleotide sequences were split into three "thirds" of length approximately 240 nt each, and each third was further split into a set of 6 or 8 overlapping degenerate oligonucleotides (see FIG. 1). Desalted degenerate oligonucleotides were obtained from Sigma Genosys and assembled into thirds by two rounds of PCR using Phusion polymerase (Finnzymes) as described (Han et al., 2004 Nature 429: 314). Standard PCR conditions were: denaturation, 10 seconds, 98° C.; annealing, 30 seconds, 45° C.; elongation, 20 seconds, 68° C. PCR products were digested at both ends with BamHI and XbaI ($1^{st}$ third), XbaI and HpaI ($2^{nd}$ third) or HpaI and EcoRI ($3^{rd}$ third), sequentially cloned into a Gateway entry vector (pGK3, see below), and sequenced after each cloning stage. In addition, some GFP fragments were obtained by PCR from the pEGFP-N2 and pGFP-N2 constructs (Kudla et al., 2006 PLoS Biol 4, e180).

One hundred twenty two $1^{st}$-third fragments, 159 $2^{nd}$-third fragments, and 65 $3^{rd}$-third fragments, for a total of 84,774 sequenced base pairs. 56% of the synthetic fragments encoded the correct protein sequence were cloned and sequenced. The average error rate of 1 per 458 base-pairs was similar to error rates obtained in standard, non-degenerate gene synthesis (Kodumal et al., 2004 Proc Natl Acad Sci USA 101: 15573). 154 synthetic GFP genes encoding the wildtype protein sequence were obtained, along with several frameshift mutants later used as controls. Some genes shared one or two synthetic fragments in common.

Bacterial Strains and Plasmids

The *E. coli* strains used for library expression were BL21 (DE3) [F⁻ ompT hsdS($r_B$-$m_B$-) dcm⁺ gal λ(DE3)] and DH5α [F'/endA1 hsdR17($r_K$-$m_K$+)supE44 thi⁻¹ recA1 gyrA(Nal$^r$) relA1 D(laclZYA-argF)U169 deoR (F80dlacD(lacZ)M15)]. The DB3.1 strain (Invitrogen) was used for cloning and amplification of Gateway expression plasmids, and the DH5α strain was used for cloning and amplification of all other plasmids. pGK3 is a Gateway entry vector. It was obtained by partially digesting pENTR-2B (Invitrogen) with XbaI and NotI, and ligating the 2701-nt fragment with annealed 5'-phosphorylated oligos: ggccctgcacattcagactcgagc (SEQ ID NO: 1) and ctaggctcgagtctgaatgtgcag (SEQ ID NO: 2). pGK8 is an IPTG-inducible Gateway expression vector with a T7 polymerase promoter. It was generated by inserting the Gateway cassette RfA (Invitrogen) into the pET15b vector (Novagen) digested with XbaI and XhoI. pGK14 and pGK16 are Gateway expression vectors with bacterial polymerase promoters. pGK14 is arabinose-inducible and was constructed by inserting the RfA cassette into pBAD33 (Guzman et al., 1995 J Bacteriol 177: 4121) digested with SmaI; while pGK16 is IPTG-inducible and was generated by inserting the RfA cassette into pTRC99a (Amann et al., 1998 Gene 69: 301) digested with EcoRI.

To clone the GFP genes from the pGK3 entry vector to pGK8, pGK14 or pGK16 expression vectors, Clonase II (Invitrogen) was used according to manufacturer's instruction. GFP genes cloned into pGK8 or pGK14 retained their original start codons, but recombination into pGK16 resulted in an in-frame fusion of 28 codons to the 5' end of the GFP genes. The tagged constructs featured weak mRNA structure near the start codon (folding energy ΔG=−6.1 kcal/mol, as compared to an average energy −9.7 kcal/mol among non-tagged genes) and low codon adaptation (CAI 0.2, as compared to an average CAI 0.3 for codons 1-28 of non-tagged genes).

RNA and Protein Measurements

Figure 2:
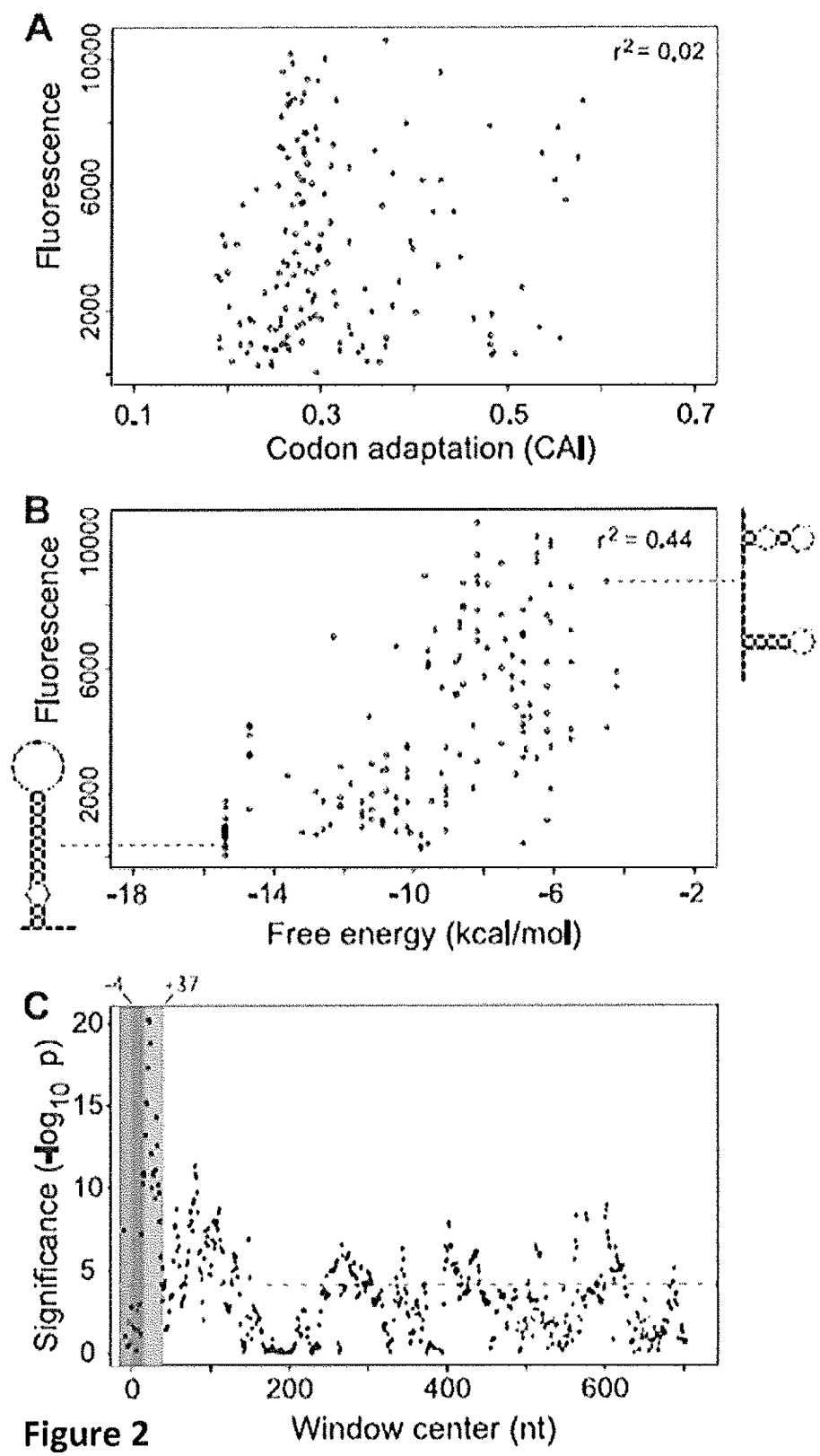
FIG. 2, comprising

Bacteria were transformed using Gateway recombination reactions. Four replicate colonies for each GFP were inoculated into LB medium with 50 ug/mL ampicillin and grown overnight to saturation in roller drums. For fluorescence measurements, cells were diluted 1:15 into 150 uL fresh medium in a 96-well plate, grown on a vibrating platform shaker (Heidolph) for 1 hour at 37° C., and induced with 1 mM IPTG (pGK8 or pGK16 plasmids) or 2% L-arabinose (pGK14 plasmids). GFP fluorescence and OD were measured in a Spectramax microplate reader (Molecular Devices). Fluorescence variation was consistent across a broad range of experimental conditions (FIG. 2).

To quantify GFP independently of its fluorescence activity, Coomassie staining and western-blotting was used. Nine GFP constructs were assayed by western blot, and 123 constructs by Coomassie. 50 uL samples of BL21 (DE3) cells expressing GFP from the pGK8' plasmid were taken 3 hours after 1 mM after IPTG induction. The cells were centrifuged, re-suspended in 50 uL distilled water, mixed with 50 uL SDS-PAGE loading buffer with SDS and 2-mercaptoethanol, and boiled for 5 minutes. The samples were then separated on 4-12% acrylamide NU-PAGE Novex Bis-Tris gels. R-250 Coomassie stained gels were scanned and quantified with the Aida image analysis software. Selected bands from noninduced cells were used to normalize GFP staining intensity between gels. Western blotting was performed using a polyclonal anti-GFP antibody (#2555 Cell Signaling) and the AlexaFluor 647-labelled donkey anti-rabbit antibody (A31573, Invitrogen). Blots were scanned using a Fuji imager and analyzed with the Aida software.

mRNA expression was analyzed by northern blotting 79 GFP constructs. For RNA measurements, overnight cultures were diluted 1:15 into 3 mL fresh medium, rotated for 1 hour at 37° C., induced with IPTG, rotated for 1.5 more hours, and 2 mL samples were centrifuged and frozen in liquid nitrogen. Cells were then lysed on ice in 0.5 mL lysis buffer (20 mM sodium acetate, 0.1% SDS, 1 mM EDTA, pH5.5), extracted twice with phenol (at 65° C.) and once with chloroform (at room temperature). RNA was then precipitated with ethanol/sodium acetate, glyoxylated, separated on 1.2% agarose/BPTE gels and transferred to positively charged nylon membranes (Amersham Biotech). 4 ug total RNA was loaded in each lane, and equal loading was confirmed by ethidium bromide staining and probing against 23S rRNA. For GFP mRNA quantification, fragments of the 5' and 3' UTRs were amplified from pGK8-GFP008 using the following primers: 5'UTR_U, ggggaattgtgagcggataa (SEQ ID NO: 3); 5'UTR_L, gtcgactgaattggttccgg (SEQ ID NO: 4); 3'UTR_U, agtggtgatatcaagcttat (SEQ ID NO: 5); 3'UTR_L, tatgctagttattgctcagc (SEQ ID NO: 6). Random-primed Klenow probes were then prepared and hybridized as described (J. Sambrook, D. Russell, Molecular cloning (Cold Spring Harbor Laboratory Press, Cold Spring Harbor, N.Y., 2001). Blots were analyzed using a Fuji imager and Aida software.

Bacterial Growth Rates

Growth rates were assessed by optical densities of cells subsequent to induction. The addition of 1 mM IPTG retarded growth in all clones, with effects ranging from a 2-fold decrease in growth rate to complete growth arrest for different GFP variants. At three hours post induction, cell densities varied 2-fold across the library. The correlation between CAI and fluorescence is even weaker after normalizing by optical density, i.e. fluorescence per cell; and the correlation between 5' folding energy and fluorescence is even stronger after normalizing by optical density.

Quantifying Rates of Protein Mis-Folding

Coomassie measurements were used to analyze the possible influence of codon adaptation on rates of protein misfolding in our experiments. For this purpose, the rate of misfolding was quantified, per GFP protein, as one minus the ratio of fluorescence (i.e. functional protein) to Coomassie (i.e. total protein). The Coomassie staining method is insensitive to changes in native protein conformation (the protein is denatured prior to electrophoresis) or to minor sequence changes caused by occasional mis-translation. Coomassie and fluorescence intensities were first converted into the same scale, mg GFP per ml, based on standardization curves obtained from serial dilutions. Both Coomassie levels and fluorescence levels exhibited linear responses to protein concentration across the range of intensities observed in our experiments. The resulting correlation between CAI and one minus fluorescence/coommassie was not significant ($r=-0.073$, $p=0.42$), indicating that codon adaptation did not correlate with mis-folding rate in our experiments.

Mis-folding rate as the ratio of mRNA (i.e. all message) to fluorescence (i.e. functional protein) was alternatively quantified. CAI was not significantly correlated with this ratio either ($r=0.09$, $p=0.42$).

Fluorescence Normalization

Fluorescence levels were normalized across experiments using a set of 12 control GFP constructs (including 2 non-fluorescent frame-shift mutants), grown in quadruplicate on every 96-well plate. A reference experiment was chosen arbitrarily, and fluorescence values from each subsequent experiment were compared to the reference. Least square linear fits were calculated, and the resulting slope and intercept values were used for normalization.

Fluorescence values were highly reproducible across biological replicates. Comparing the 10 non-mutant control GFPs across 18 plates resulted in an average correlation coefficient of 0.979. Similarly, a non-parametric ANOVA indicated a significantly larger fluorescence variance across GFP constructs than across replicates (p<1E-15).

Single-Mutation GFP Constructs

A separate silent mutagenesis experiment was performed on the first five codons of one of the genes, GFP_020. Five cases in which a single silent mutation altered 5' folding energy, by at least 3.9 kcal/mol was identified. Among the mutants, the gene with weaker predicted 5' structure had higher expression in four cases (by 18%, 35%, 49% and 83%), and lower expression in one case (by 9%). A pair of genes that differed by two silent sites (nt 6 and 15) was also obtained. Again, these mutations had a substantial effect on the predicted 5' folding energies (dG=−11.7 and dG=−7.7, respectively), and the construct with stronger structure exhibited a much lower protein level (fl=2473 and fl=8051, respectively). These results confirm that the relationship between folding energy and expression extends to constructs that differ by only a few mutations in their 5' region. See Table 1

TABLE 1

Pairs of GFP genes differing by a single mutation:

| nucleotides 1-15 (seq 1) | nucleotide substitution (seq 1 -> seq2) | energy change (seq2- seq 1) | fl change (seq2- seq 1)/ seq 1 |
|---|---|---|---|
| ATGGTGAGCAAGGGG SEQ ID NO: 7 | G6 -> T | 6.2 kcal/mol | 35% |
| ATGGTGAGCAAGGGA SEQ ID NO: 8 | G6 -> T | 6.2 kcal/mol | 18% |
| ATGGTGAGCAAGGGG SEQ ID NO: 9 | C9 -> T | 3.9 kcal/mol | 49% |
| ATGGTGAGCAAGGGG SEQ ID NO: 10 | G6 -> C | 6.1 kcal/mol | -9% |
| ATGGTGAGCAAGGGC SEQ ID NO: 11 | G6 -> T | 4 kcal/mol | 83% |

Statistical Analyses

All statistical analyses were performed in the R software package (R Development Core Team, R: A language and environment for statistical computing (R Foundation for Statistical Computing, Vienna, Austria, 2005)). Correlations reported in the main text are quantified by the Spearman rank correlation coefficient and its associated p-value.

The frequency of rare codon pairs was calculated using the CPB metric of Coleman et al. (Coleman et al., 2008 Science 320: 1784). The frequency of rare pairs was not significantly correlated with fluorescence (r=0.07, p=0.35). Similarly, the palindromic sequence CTAG is strongly underrepresented in the E. coli genome (Burge et al., 1992 Proc Natl Acad Sci USA 89: 1358), but the frequency of this motif in a GFP gene did not correlate with its fluorescence (r=−0.12, p=0.16). For the multiple regressions, sequence-derived covariates associated with each GFP construct included: the codon adaptation index (Sharp et al., Nucleic Acids Res 15: 1281) calculated for the entire or partial coding sequence; the number of rare codons (sites with CAI<0.1) in the coding sequence; the number of pairs of consecutive rare codons; the length of the longest stretch of consecutive rare codons; the GC3 content of the coding sequence; the number of predicted rho-independent transcription termination signals, calculated using the RNAMotif program (Lesnik et al., 2001 Nucleic Acids Res 29: 3583); the propensity for conformation changes into Z-DNA, calculated using the Zhunt program (Ho et al., 1986 Embo J 5: 2737); the number of potential RNAse E cleavage sites, calculated as in (Bernstein et al., 2002 Proc Natl Acad Sci USA 99: 9697); the minimum free energy of predicted mRNA secondary structure, for the entire gene sequence or portions of the sequence, calculated using the hybrid-ss-min program (Markham et al., 2005 Nucleic Acids Res 33: W577) (version 3.4, NA=RNA, t=37, [Na+]=1, [Mg++]=0, max-loop=30, prefilter=2/2); a categorical variable indicating whether or not the first third of the GFP was synthesized using the "optimized" EGFP sequence (gi: 1543069).

A multiple regression was performed in order to quantify the relative importance of the various predictor variables in determining rank fluorescence levels. The output of this regression, shown below in Table 2, highlights the predominant influence of mRNA folding energy near the start of the GFP sequence (nt −4 to +37):

TABLE 2

Multiple Regression

| Coefficients | Estimate | Std Error | T | Pr(>|t|) |
|---|---|---|---|---|
| FreeEnergy −4 to +37 | 7.462 | 1.181 | 6.318 | 3.20E−09 |
| CAI | 152.911 | 136.360 | 1.121 | 0.26402 |
| GC3 | −56.326 | 51.445 | −1.095 | 0.27543 |
| nsites_lowCAI | 2.575 | 1.155 | 2.230 | 0.02731 |
| npairs_lowCAI | −5.324 | 1.798 | −2.962 | 0.00358 |
| nstretches_lowCAI | 2.746 | 4.070 | 0.675 | 0.501 |
| longeststretch_lowCAI | 5.551 | 4.143 | 1.340 | 0.18235 |
| FirstThirdEGFP | −17.627 | 9.998 | −1.763 | 0.08002 |
| Terminator.Predicted | 0.729 | 3.362 | 0.217 | 0.82868 |
| zDNA.Predicted | 1.269 | 8.023 | 0.158 | 0.87453 |
| N_RNAaseE | −0.836 | 0.320 | −2.614 | 0.00991 |

Residual standard error: 29.42 on 142 degrees of freedom. Multiple R-Squared: 0.5961, Adjusted R-squared: 0.5649. F-statistic: 19.05 on 11 and 142 DF, p-value: <2.2e-16.

In order to control for possible confounding effects arising from collinearity of predictor variables, an analogous principal component regression was also performed. The four principal components that explained the most variance in rank fluorescence are shown below. The tables below indicate the loadings of the predictor variables on each of the four principal components, the amount of variance in fluorescence levels explained by each component, and the total amount of variance in fluorescence explained by each predictor variable, summed across all components (as in (Plotkin et al., 2007 Mol Biol Evol 24: 1113):

TABLE 3

Principal Component Regression

| Loadings | Comp1 | Comp2 | Comp3 | Comp4 |
|---|---|---|---|---|
| FreeEnergy −4 to +37 | 0.956 | 0 | 0 | 0.005 |
| CAI | 0 | 0 | 0 | 0.001 |
| GC3 | 0 | 0 | 0 | 0 |
| nsites_lowCAI | 0.001 | 0.249 | 0.64 | 0 |
| npairs_lowCAI | 0.027 | 0.07 | 0.047 | 0 |
| nstretches_lowCAI | 0.008 | 0.003 | 0.001 | 0 |
| longeststretch_lowCAI | 0.001 | 0.001 | 0 | 0.014 |
| FirstThirdEGFP | 0.005 | 0 | 0 | 0.977 |

TABLE 3-continued

| Principal Component Regression | | | | |
|---|---|---|---|---|
| Terminator.Predicted | 0.002 | 0 | 0 | 0 |
| zDNA.Predicted | 0 | 0 | 0 | 0.002 |
| N_RNAaseE | 0 | 0.676 | 0.312 | 0 |

| Component | % Variance Explained: |
|---|---|
| Comp1 | 47.23 |
| Comp2 | 4.99 |
| Comp3 | 4.15 |
| Comp4 | 1.55 |
| Comp5 | 0.55 |
| Comp6 | 0.37 |
| Comp7 | 0.24 |
| Comp8 | 0.22 |
| Comp9 | 0.11 |
| Comp10 | 0.11 |
| Comp11 | 0.02 |

| Predictor Variable | Total % Variance Explained |
|---|---|
| FreeEnergy −4 to +37 | 45.175 |
| CAI | 0.372 |
| GC3 | 0.22 |
| nsites_lowCAI | 3.972 |
| npairs_lowCAI | 1.958 |
| nstretches_lowCAI | 0.545 |
| longeststretch_lowCAI | 0.542 |
| FirstThirdEGFP | 1.755 |
| Termintor.Predicted | 0.282 |
| zDNA.Predicted | 0.114 |
| N_RNAaseE | 4.68 |

Multiple regressions of rank fluorescence against GC3, CAI, and free energy associated with mRNA folding were also performed, each calculated in a window from nt −4 through nt 37. (The "A" in ATG is assigned nt 0.) Both the standard and principal component versions of this regression indicate that mRNA folding energy is the dominant determinant of expression levels:

TABLE 4

| Multiple Regression | | | | |
|---|---|---|---|---|
| Coefficients | Estimate | Std Err | T | Pr(>|t|) |
| FreeEnergy −4 to +37 | 0.45472 | 0.09016 | 5.043 | 1.30E−06 |
| GC3 −4 to +37 | −0.29785 | 0.09296 | −3.204 | 0.001655 |
| CAI −4 to +37 | 0.1078 | 0.06272 | 1.719 | 0.087684 |

Residual standard error: 31.48 on 150 degrees of freedom
Multiple R-Squared: 0.5115
Adjusted R-squared: 0.5017 F-statistic: 52.35 on 3 and 150 DF, p-value: <2.2e-16

TABLE 5

| Principal Component Regression | | | |
|---|---|---|---|
| LOADINGS | Comp1 | Comp2 | Comp3 |
| FreeEnergy −4 to +37 | 0.997 | 0.001 | 0.002 |
| GC3 −4 to +37 | 0.003 | 0.471 | 0.526 |
| CAI −4 to +37 | 0.000 | 0.527 | 0.473 |

| Component | % Variance Explained: |
|---|---|
| Comp1 | 42.24 |
| Comp2 | 6.12 |
| Comp3 | 0.6 |

TABLE 5-continued

| Principal Component Regression | |
|---|---|
| Predictor Variable | Total % Variance Explained |
| FreeEnergy −4 to +37 | 42.118 |
| GC3 −4 to +37 | 3.322 |
| CAI −4 to +37 | 3.508 |

Multiple regressions of fluorescence levels against mRNA levels, folding energy, and CAI were also performed. Folding energy explained significantly more variation in fluorescence levels than mRNA levels explained:

TABLE 6

| Multiple Regression | | | | |
|---|---|---|---|---|
| Coefficients | Estimate | Std Err | t | Pr(>|t|) |
| FreeEnergy −4 to +37 | 0.47425 | 0.08785 | 5.399 | 7.58E−07 |
| Northern | 0.37767 | 0.08723 | 4.33 | 4.56E−05 |
| CAI | 0.1469 | 0.08293 | 1.771 | 0.0806 |

Residual standard error: 16.68 on 75 degrees of freedom
Multiple R-Squared: 0.4918,
Adjusted R-squared: 0.4715 F-statistic: 24.19 on 3 and 75 DF, p-value: 4.693e-11

TABLE 7

| Principal Component Regression | | | |
|---|---|---|---|
| Loadings | Comp1 | Comp2 | Comp3 |
| FreeEnergy −4 to +37 | 0.54 | 0.017 | 0.443 |
| Northern | 0.401 | 0.233 | 0.366 |
| CAI | 0.059 | 0.75 | 0.191 |

| Component | % Variance Explained |
|---|---|
| Comp1 | 38.46 |
| Comp2 | 11.23 |
| Comp3 | 3.75 |

| Predictor Variable | Total % Variance Explained |
|---|---|
| FreeEnergy −4 to +37 | 22.636 |
| Northern | 19.41 |
| CAI | 11.354 |

Sliding Window Analysis of Local Folding Energy and Fluorescence

The relationship between fluorescence intensity and folding energy in sliding windows across the GFP sequence was analyzed. A window of size 42 bases was chosen, and the location of the window was slid in increments of three bases across the gene sequence, including 5' UTR. The Spearman correlation coefficient between predicted folding energy within each window and fluorescence intensity, across the library of GFP genes was calculated. Many regions of highly significant positive correlations, including the region from nt −4 to nt 37 for which folding energy explains nearly half of the variation in fluorescence intensity (r=0.665, p<1E-15, FIG. 2B) was identified.

The results of the experiments presented in this Example are now described.

The theory of codon bias posits that preferred codons correlate with the abundances of iso-accepting tRNAs (Zuckerkandl et al., 1965 J. Theor. Biol. 8: 357; Ikemura, 1985 Mol. Biol. Evol. 2: 13) and thereby increase translational efficiency (Ikemura, 1981 J. Mol. Biol. 151: 389) and accuracy (Akashi, 1994 Genetics 136: 927). Recent experiments have revealed other effects of silent mutations (Parmley et al., 2007 Bioessays 29: 515; Kimchi-Sarfaty et al., 2007 Science 315: 525; Nackley et al., 2006 Science 314: 1930). A library of green fluorescent protein (GFP) genes that varied randomly in their codon usage, but encoded the same amino acid sequence was synthesized. By placing these constructs in identical regulatory contexts and measuring their expression, the effects of synonymous variation on gene expression were isolated.

Figure 4:
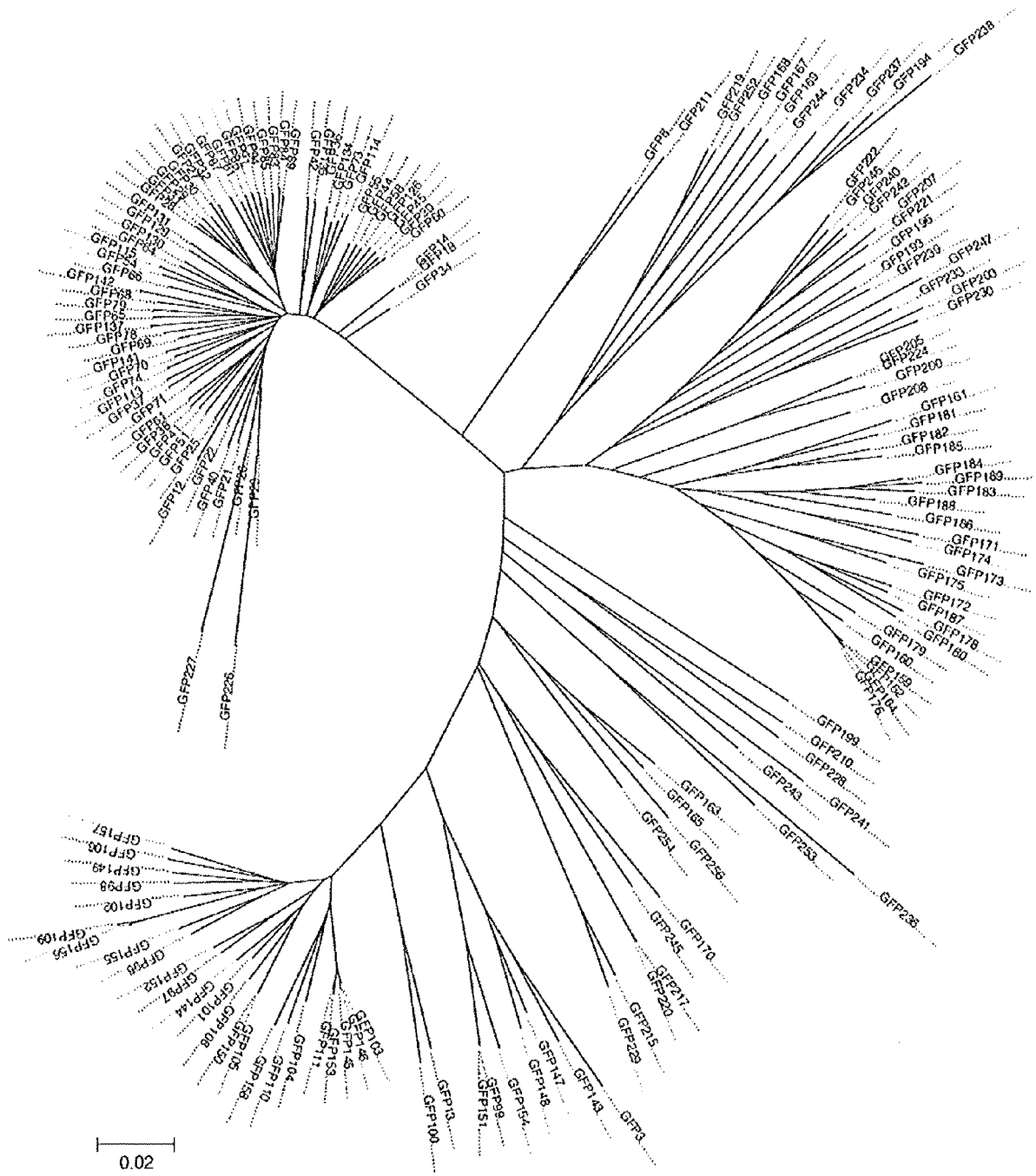
FIG. 4 is a schematic depicting a distance tree of synthetic GFP genes.
Figure 5:
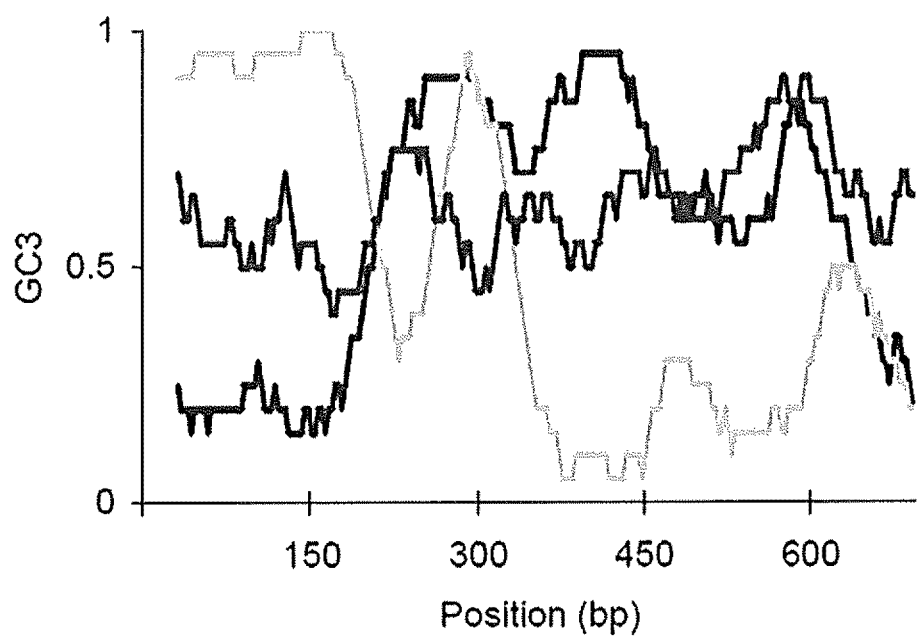
FIG. 5 is an image depicting GC content in a moving window across three example GFP constructs.

The GFP gene consists of 240 codons. For 226 of these codons, random silent mutations were introduced in the third base position, while keeping the first and second positions constant (FIG. 1A). The resulting synthetic GFP constructs differed by up to 180 silent substitutions, with an average of 114 substitutions between pairs of constructs (FIG. 1B and FIGS. 4 and 5). The range of third-position GC content (GC3) across the library of constructs encompassed virtually all (99%) of the GC3 values among endogenous *Escherichia coli* genes, and the variation in the codon adaptation index (CAI) (Sharp et al., 1987 Nucleic Acids Res. 15: 1281) contained most (96%) of the CAI values of *E. coli* genes (FIG. 1).

Figure 6:
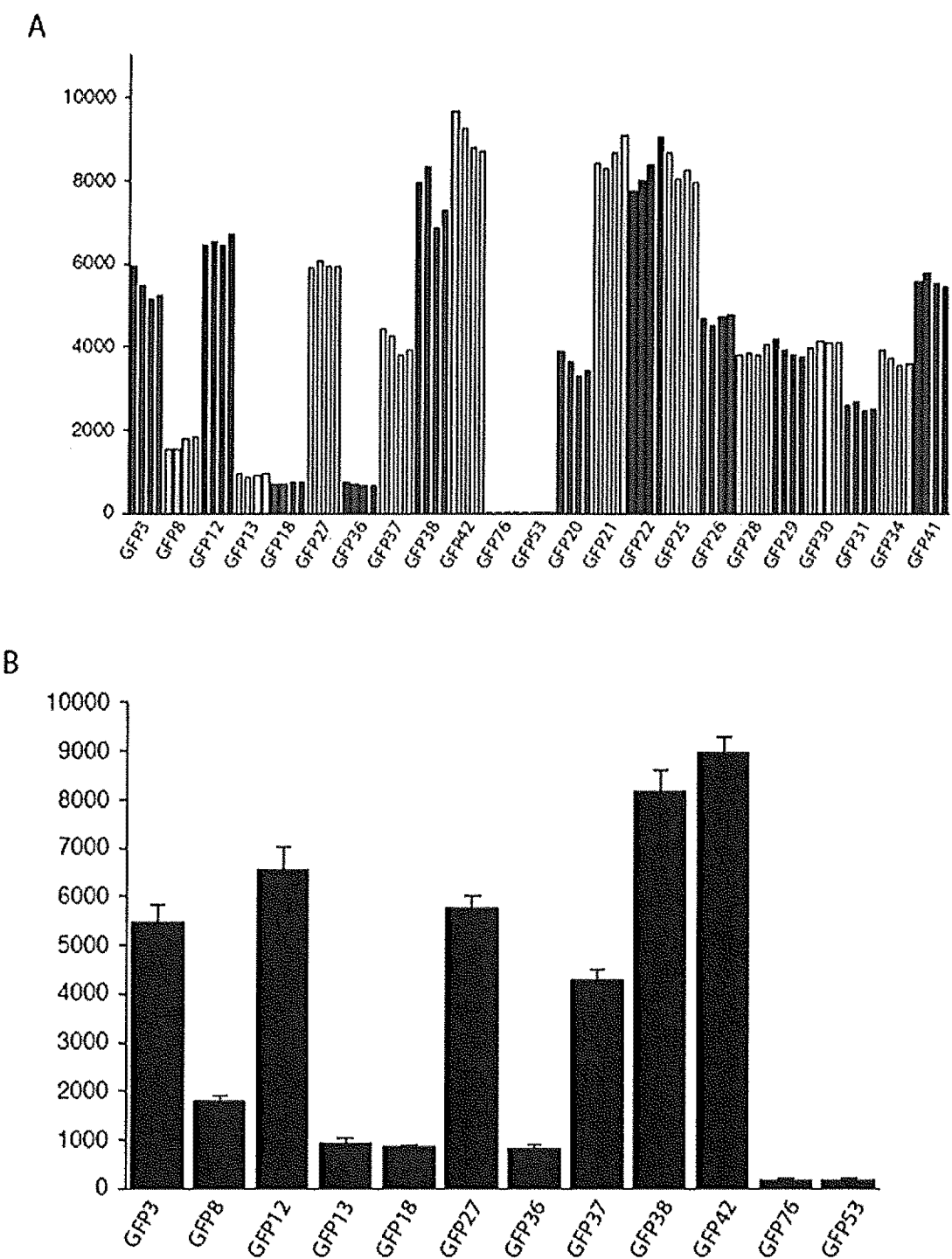
FIG. 6, comprising
Figure 7:
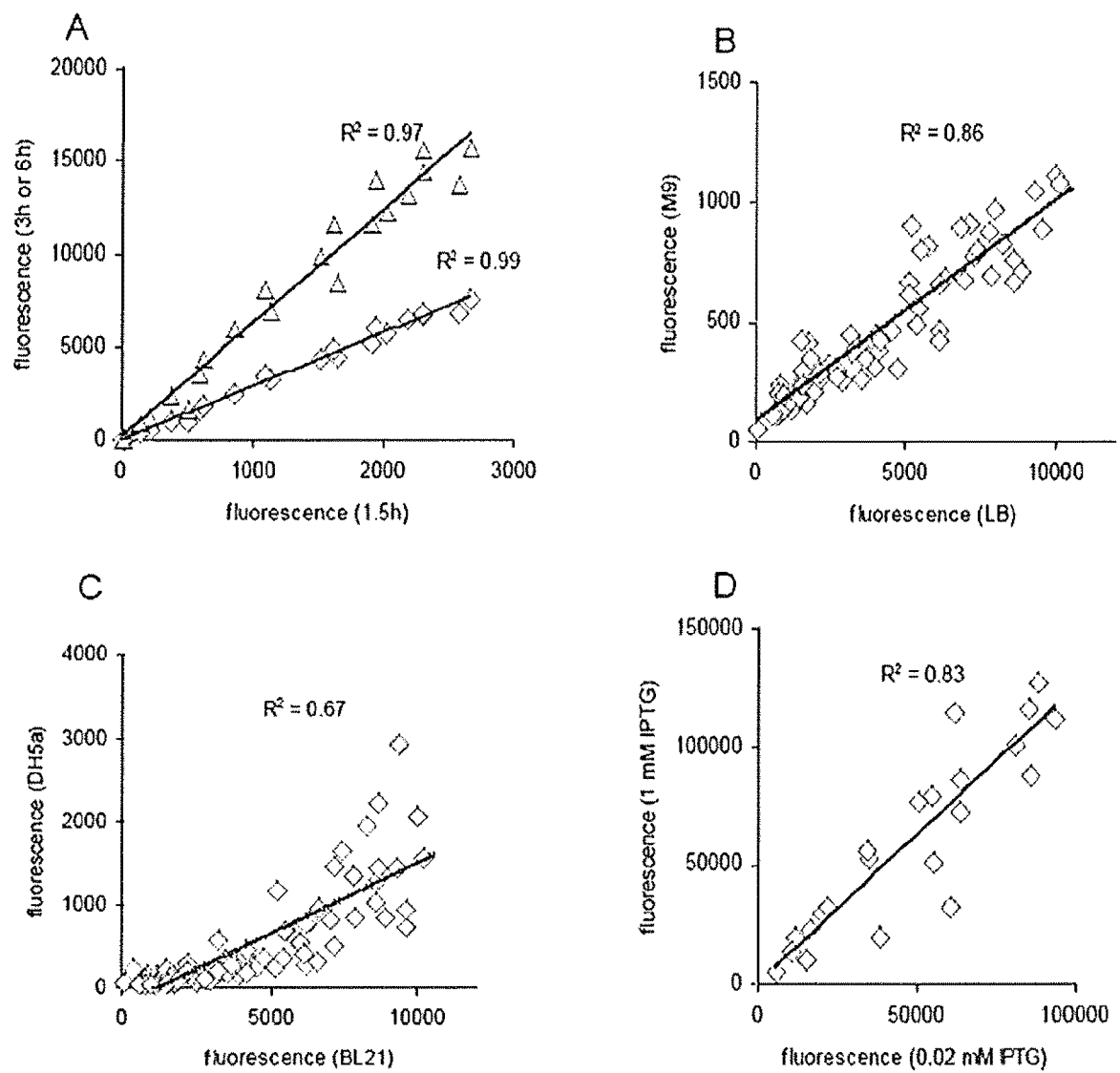
FIG. 7, comprising
Figure 8:
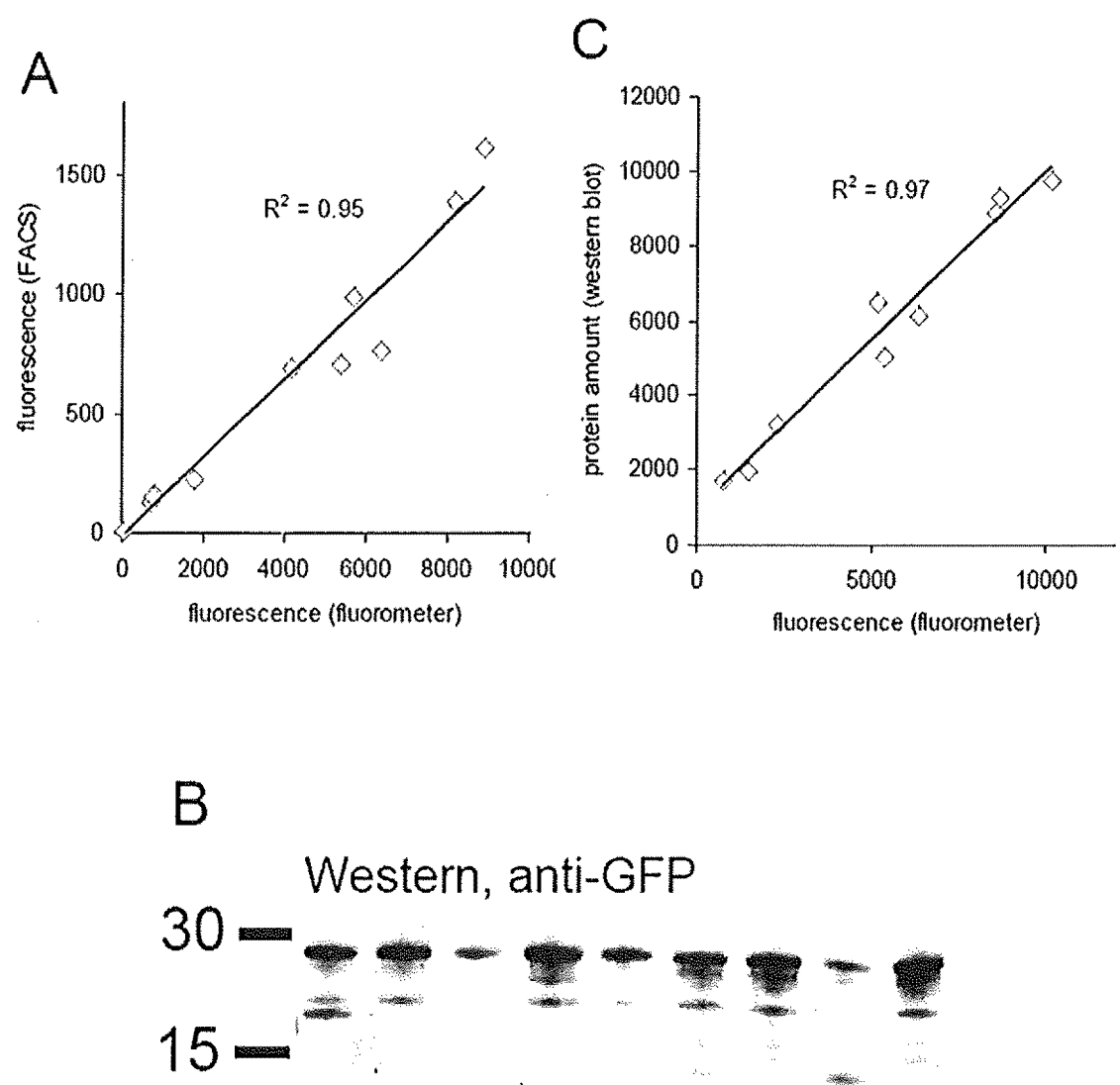
FIG. 8, comprising

The GFP genes were expressed in *E. coli* using a T7-promoter vector, and expression was quantified using spectrofluorometry. Fluorescence levels varied 250-fold across the library, and were highly reproducible for each GFP construct (Spearman $r=0.98$ between biological replicates) (FIG. 6). Fluorescence variation was consistent across a broad range of experimental conditions (FIG. 7). An alternative plasmid with bacterial promoter reduced overall expression levels, but the correlation between the two expression systems remained high ($r=0.9$) (FIG. 7). A similar pattern of fluorescence variation was observed in fluorescence-activated cell sorting measurements (FIG. 8). Because the encoded protein sequence was identical for all genes, fluorescence variation was attributed to differences in protein levels. This was confirmed by strong correlations between fluorescence and total GFP levels in Western blots (FIG. 8) and Coomassie staining ($r=0.9$, $P<10^{-15}$).

To test the theory that *E. coli* translation rates and eventual protein levels depend on the concordance between codon usage and cellular tRNA abundances (Gustafsson et al., 2004 Trends Biotechnol. 22: 346; Lithwick et al., 2003 Genome Res. 13: 2665; Rosenberg et al., 1993 J. Bacteriol. 175: 716), codon usage was compared to fluorescence among the 154 synonymous GFP variants. Notably, neither of the two most common measures of codon bias, the CAI or the frequency of optimal codons (Ikemura, 1981 J. Mol, Biol. 151: 389), was significantly correlated with fluorescence levels ($r=0.14$, $P=0.09$, and $r=0.11$, $P=0.16$, respectively) (FIG. 2A). Moreover, some of the most highly expressed genes featured low CAI and vice versa.

Although codon adaptation near the 5' terminus is considered particularly important for expression (Rosenberg et al., 1993 J. Bacteriol. 175: 716; Gonzalez de Valdivia et al., 2004 Nucleic Acids Res. 32: 5198), the CAI value of the first 42 bases in a GFP gene was not significantly correlated with the gene's fluorescence intensity ($r=0.1$, $P=0.2$). Similarly, the number of rare codons (sites with CAI<0.1) in a sequence was not significantly correlated with fluorescence ($r=-0.02$, $P=0.7$), and neither was the number of pairs of consecutive rare codons ($r=-0.14$, $P=0.09$). Although specific consecutive codon pairs have been proposed to influence translation (Boycheva et al., 2003 Bioinformatics 19: 987; Coleman et al., 2008 Science 320, 1784), the frequency of such rare pairs in a gene was not significantly correlated with its fluorescence ($r=0.07$, $P=0.35$).

Figure 9:
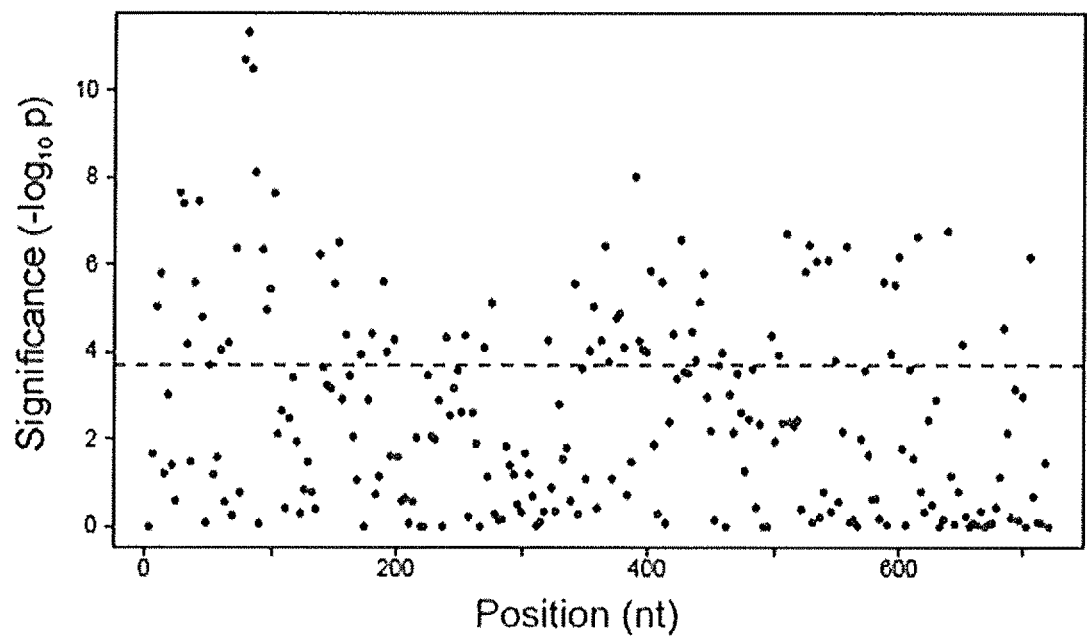
FIG. 9 is an image depicting site-specific influence of silent nucleotide variation on protein levels, across the GFP sequence. At each silent position we plot the statistical significance (negative log p-value) of a regression comparing nucleotide identity and fluorescence levels among the 154 GFP constructs. At the codon positions above the dashed line, the choice of G, C, A, or T in the third base-pair was significantly correlated with fluorescence, after Bonferroni correction for multiple hypotheses.
Figure 10:
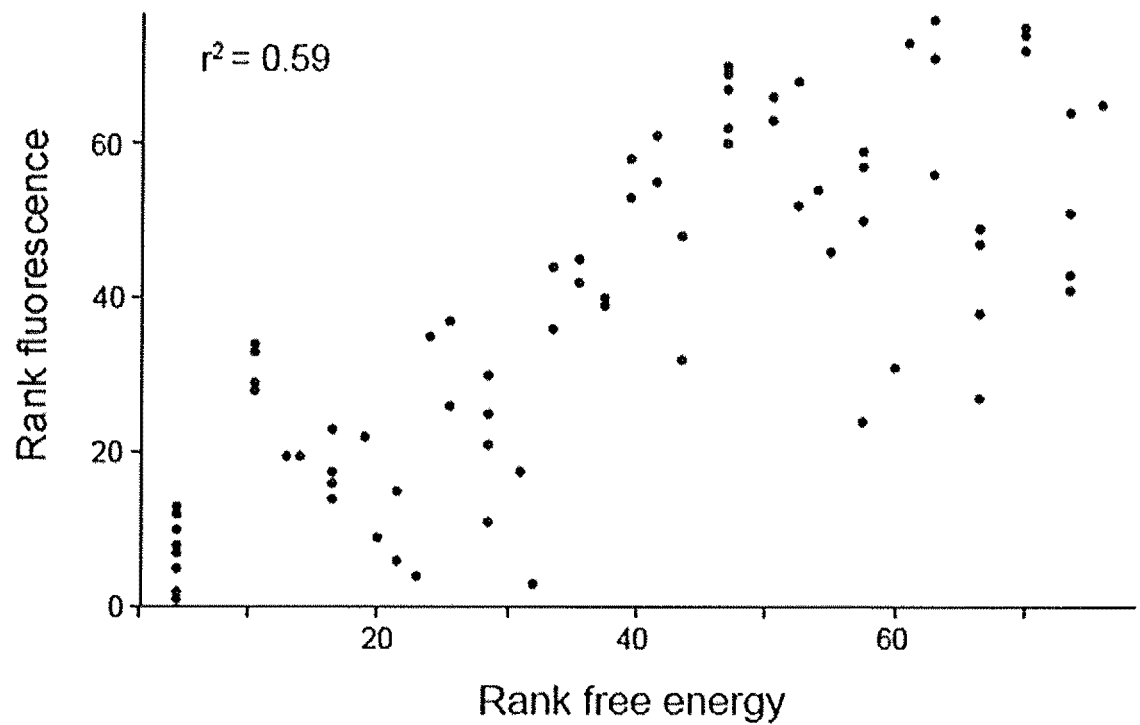
FIG. 10 is an image depicting free energy and gene expression under a bacterial promoter. The relationship between rank 5' mRNA folding energy and rank fluorescence among pGK14-GFP constructs (Spearman r=0.77 p<4E-16).

Statistical analyses of which nucleotide positions influenced gene expression (FIG. 9) indicated the importance of local sequence patterns, as opposed to global codon bias. This pattern is consistent with studies of base content (Andersson et al., 1990 Microbiol. Rev. 54: 198; Eyre-Walker et al., 1993 Nucleic Acids Res. 21: 4599), which suggest that mRNA structure may shape expression levels (Hall et al., 1982 Nature 295: 616; Griswold et al., 2003 Protein Expr. Puff, 27: 134; Qing et al., 2003 J. Mol. Microbiol. Biotechnol. 6: 133; Duan et al., 2003 Hum. Mol. Genet. 12: 205). Therefore, for each GFP construct, the predicted minimum free energy associated with the secondary structure of its entire mRNA or specific regions of its mRNA was computed. The folding energy of the entire mRNA was not significantly correlated with fluorescence ($r=0.16$, $P=0.051$), but the folding energy of the first third of the mRNA was strongly correlated: mRNAs with stronger structure produced lower fluorescence ($r$ 0.60, $P<10^{-15}$). A moving window analysis identified a region, from nucleotide (nt) −4 to +37 relative to start, for which predicted folding energy explained 44% of the variation in fluorescence levels across the GFP library ($r=0.66$, $P<10^{-15}$) (FIG. 2B). The same folding energies explained 59% of fluorescence variation when constructs were expressed using a bacterial promoter ($r=0.77$, $P<4\times10^{-16}$) (FIG. 10). mRNA folding also correlated with fluorescence in a separate analysis of GFP constructs differing by single mutation.

Figure 11:
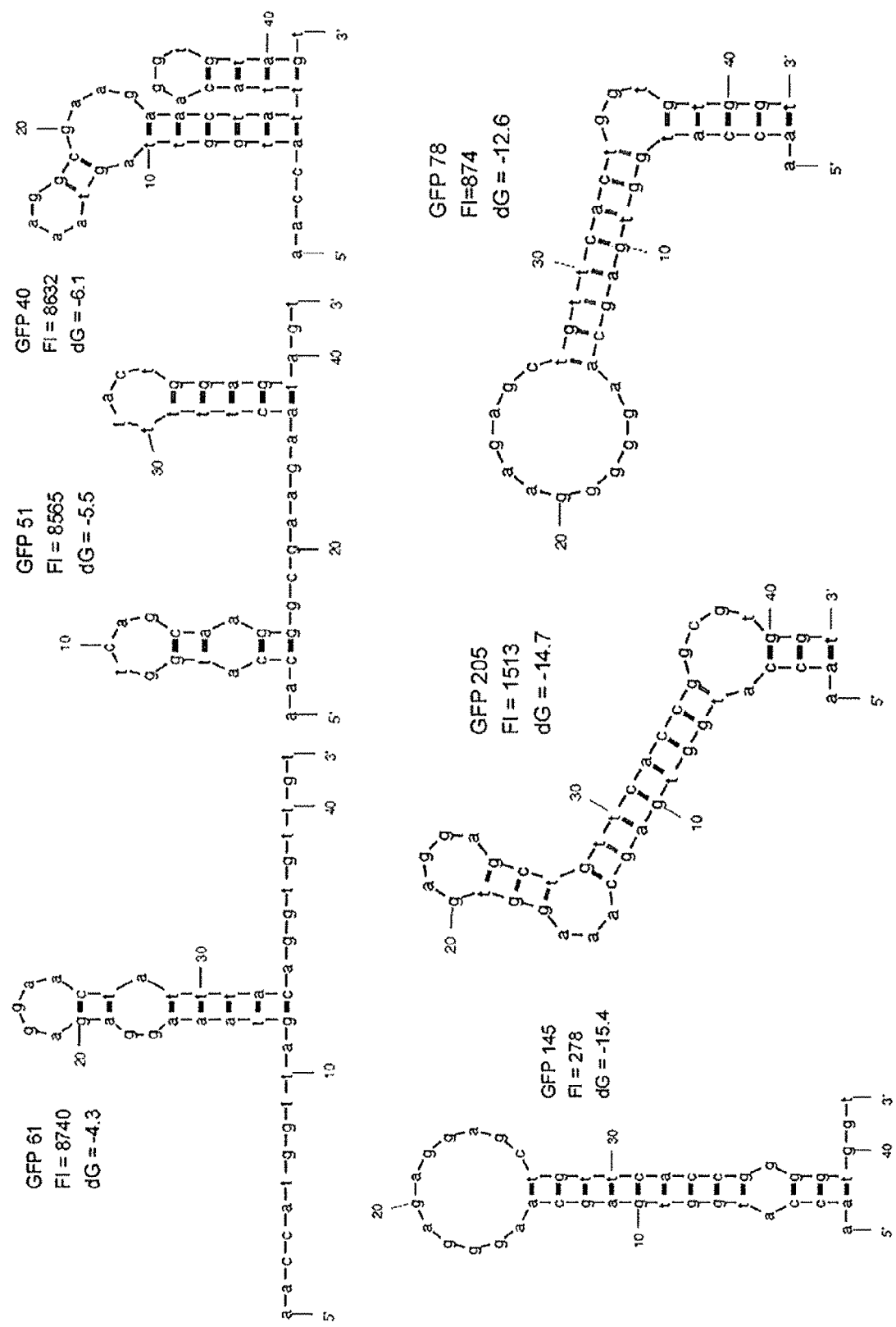
FIG. 11 is a schematic of predicted mRNA secondary structures for representative examples of GFP constructs. The figure shows three GFP constructs with high fluorescence (top row), and three GFP constructs with low fluorescence (bottom row). Along with the secondary structure of region nt −4 through nt +37, the figure also indicates the free energy of each secondary structure (kcal/mol) and the fluorescence of the corresponding GFP construct. Note that GFP constructs expressed at low levels feature mRNA structures with large hairpin loops, whereas GFP constructs expressed at high levels feature structures with many unpaired nucleotides.

The strong correlation between mRNA folding and fluorescence suggests the simple mechanistic explanation that tightly folded messages obstruct translation initiation and thereby reduce protein synthesis (Kozak, 2005 Gene 361: 13). Predicted mRNA structures for highly expressed GFPs characteristically contained many unpaired nucleotides near the start codon, whereas constructs expressed at low levels featured long hairpin loops (FIG. 2B and FIG. 11), consistent with known obstructions to initiation (Kozak, 2005 Gene 361: 13). The region of strongest correlation between folding energy and expression did not overlap with the Shine-Dalgarno (SD) sequence, which suggested that SD occlusion by secondary structure (Kozak, 2005 Gene 361: 13; de Smit et al., 1990 Proc, Natl. Acad. Sci. U.S.A. 87: 7668) did not play a major role in inhibiting expression, probably because the constructs used contained no noncoding mutations. By contrast, the region of strongest effect overlapped significantly with the 30-nt ribosome-binding site centered around the start codon (FIG. 2C).

In a multiple regression, mRNA folding energy near the start codon (nt −4 through +37) explained nearly 10 times as much variation in expression levels as any other predictor variable, including the global GC content, CAI, the number of rare-codon sites or consecutive pairs, the length of the longest rare-codon stretch, the number of predicted transcription termination signals, the propensity for conformation changes into Z-DNA, and the number of predicted ribonuclease (RNase) E cleavage sites. RNase E cleavage sites tended to reduce expression, as expected (Mudd et al., 1990 Mol. Microbiol. 4: 2127), and explained 4.7% of fluorescence variation.

Although global GC content was not significantly correlated with fluorescence ($r=-0.031$, $P=0.7$), GC content near the start codon was strongly correlated. But this was likely mediated by mRNA secondary structure; GC content was itself correlated with folding energy, and folding energy explained 10 times as much variation in fluorescence as was explained by GC content.

Figure 12:
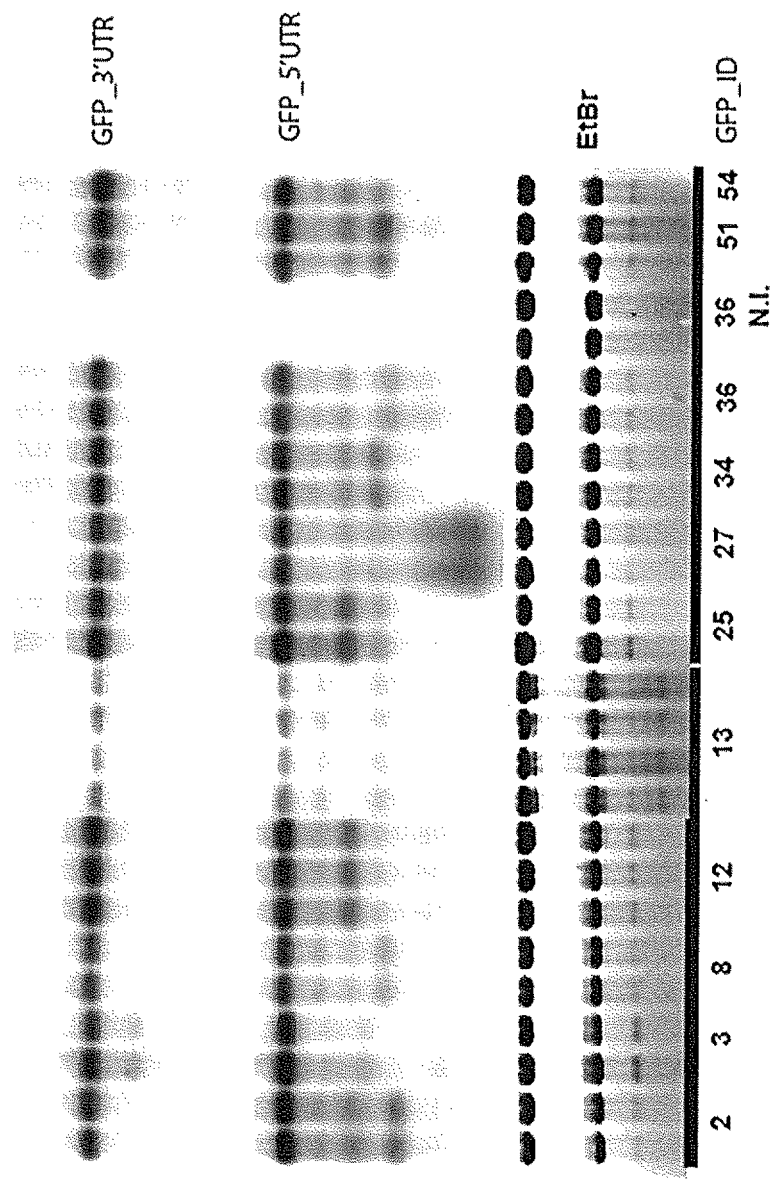
FIG. 12 is a Northern blot analysis of GFP mRNA levels. mRNA from duplicate pGK8-GFP clones was isolated and analyzed by northern blotting, using probes against GFP 5'UTR and 3'UTR sequences common to all clones. Bottom panel, ethidium bromide staining of total cellular RNA. Note the variable degradation patterns of mRNAs across different GFP constructs. NI denotes no inducer.

GFP mRNA levels, as quantified by Northern blotting, varied across the library, but the extent of mRNA variation was three times smaller than that of corresponding fluorescence variation. 3'-truncated mRNA species that differed among GFP variants, which likely reflected different stabilities of mRNA degradation intermediates was observed (FIG. 12). mRNA levels were highly correlated with fluorescence (r=0.53) and also with folding energy near the start codon (r=0.33). These relations are consistent with the hypothesis that secondary structure influences both mRNA and protein levels through occlusion of ribosome subunit binding. Reduced ribosome binding increases mRNA exposure to nuclease digestion, which in turn decreases stability (lost et al., 1995 EMBO J. 14: 3252).

Bacterial growth rates were strongly influenced by the codon usage of the expressed GFP construct. Elevated CAI was correlated with faster growth (r=0.54, $P<9\times10^{-13}$), whereas 5' mRNA folding energy showed no significant correlation with growth (r=0.12, P=0.15). These results support the hypothesis that low codon adaptation in an overexpressed gene decreases cellular fitness (Andersson et al., 1990 Microbiol. Rev. 54: 198), probably because retarded elongation sequesters ribosomes on the GFP mRNA and thereby hinders translation of essential mRNAs. The growth rate data could alternatively be explained by the hypothesis that high codon adaptation reduces the rate of deleterious protein misfolding (Kimchi-Sarfaty et al., 2007 Science 315: 525; Drummond et al., 2005 Proc. Natl. Acad. Sci. U.S.A. 102: 14338; Stoletzki et al., 2007 Mol. Biol. Evol. 24: 374). The results presented herein indicate that CAI was not correlated with the degree of misfolding, whether it was quantified by the ratio of Coomassie to fluorescence or by the ratio of mRNA to fluorescence.

Figure 3:
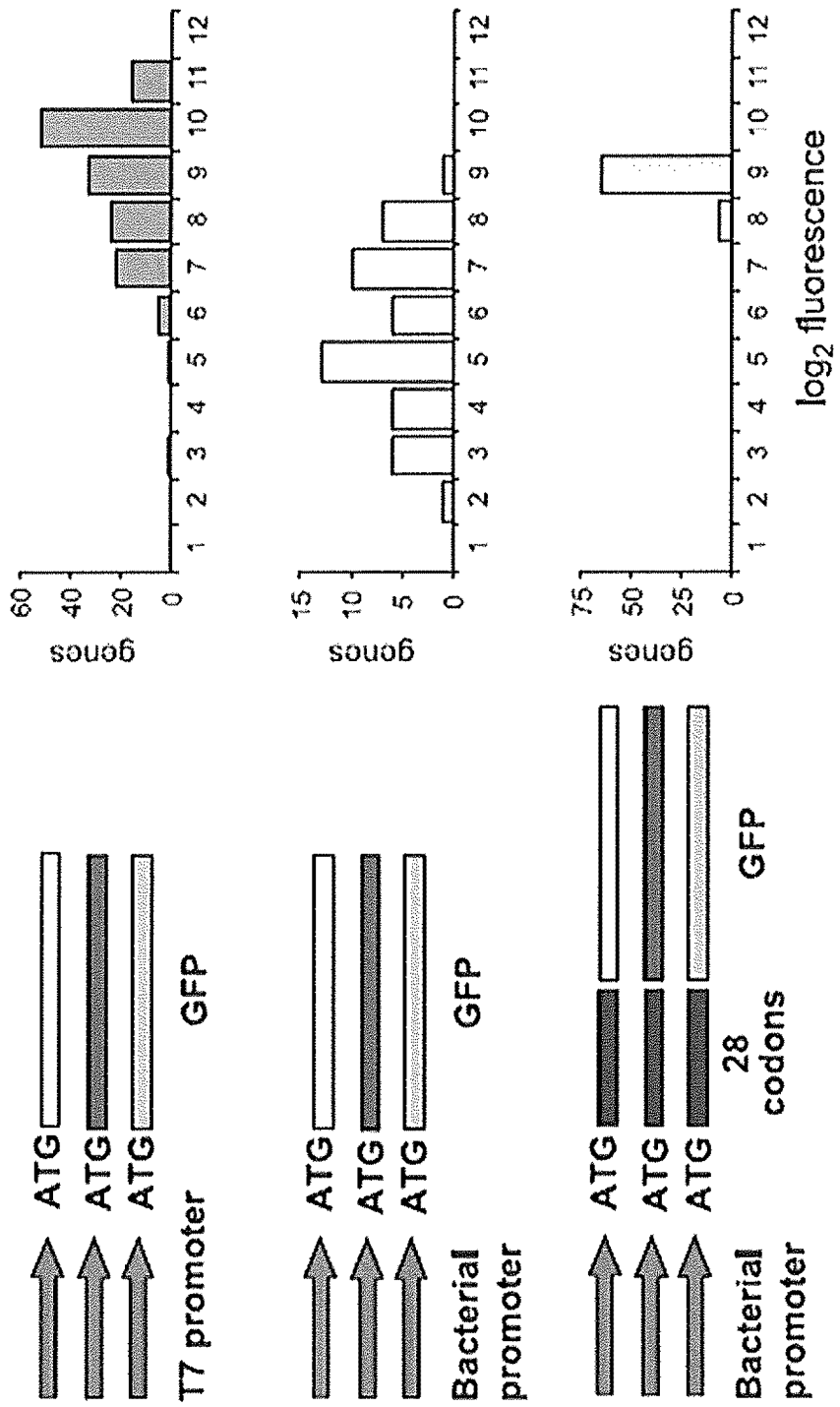
FIG. 3 depicts the expression levels of alternative GFP constructs. The distribution of $\log_2$ normalized fluorescence levels for (top) pGK8 (T7 promoter, no leader sequence), (middle) pGK14 ($P_{BAD}$ bacterial promoter, no leader sequence) and (bottom) pGK16 (trp-lac bacterial promoter, 28-codon leader sequence) expression vectors. Fluorescence varied substantially when expressed using T7 or bacterial promoter. The addition of a 28-codon leader sequence with low secondary structure produced uniformly high expression levels.

The disclosure presented herein support the following prediction: Adding a stretch of codons with weak mRNA structure to the 5' end of a gene with originally strong structure should increase expression, even if the additional codons have low CAI. To test this prediction, a 28-codon tag was fused to the 5' terminus of 72 GFP constructs. The tagged constructs, which featured weak mRNA secondary structure and low CAI, produced consistently high expression, including those GFPs poorly expressed in nontagged form (FIG. 3). These results suggest that endogenous E. coli genes may have undergone selection for weak 5' secondary structure. Consistent with this hypothesis, it was found that the predicted secondary structures for the 4294 E. coli genes are significantly weaker near their start codons (nt −4 to +37) than immediately downstream (nt +38 to +79; Wilcoxon $P<10^{-15}$).

The disclosure presented herein systematically quantified the effects of synonymous nucleotide variation on gene expression in E. coli, on the basis of unbiased sequences that control for regulatory context. The data reveal a predominant role for mRNA structure around the ribosomal binding site in shaping mRNA and protein levels. By contrast, neither local nor global codon bias had significant effects on mRNA or protein levels. This finding is consistent with the view that translation initiation, not elongation, is rate-limiting for gene expression (Jacques et al., 1990 Mol. Microbiol. 4: 1063), but it seems to contradict the well-known correspondence between codon bias and expression level for endogenous genes (Lithwick et al., 2003 Genome Res. 13: 2665; Ghaemmaghami et al., 2003 Nature 425: 737). There is a simple explanation to this apparent contradiction, which reverses the arrow of causality between codon adaptation and gene expression. In one view, high CAI induces strong protein expression (Gustafsson et al., 2004 Trends Biotechnol. 22: 346; Lithwick et al., 2003 Genome Res, 13: 2665; Rosenberg et al., 1993 J. Bacteriol. 175: 716), whereas arguably strong expression induces selection for high CAI. Unlike genome-wide correlations between CAI and expression levels [e.g. (Lithwick et al., 2003 Genome Res. 13: 2665)], the experiments disclosed herein control for noncoding regulation and, thus, can distinguish between these two alternatives.

Without wishing to be bound by any particular theory, it is believed that the correspondence between codon adaptation and expression level among endogenous E. coli genes arises from selection to make translation efficient at a global level, rather than at the level of individual genes. High CAI increases the elongation rate, but because initiation is rate-limiting in translation, elongation rate does not significantly affect expression. On the other hand, rapid elongation sequesters fewer ribosomes on the message, thereby increasing the total rate of protein synthesis and accelerating cell growth. A similar model for codon preference has been proposed by Andersson and Kurland (Andersson et al., 1990 Microbiol. Rev. 54: 198). Well-adapted codons could also confer a metabolic advantage by reducing the load of misfolded proteins (Drummond et al., 2005 Proc. Natl. Acad. Sci. U.S.A. 102: 14338; Stoletzki et al., 2007 Mol. Biol. Evol. 24: 374). In either case, increasing a gene's codon adaptation should not increase its expression. High codon adaptation in a gene should, however, improve cellular fitness to an extent that depends on its expression level.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated nucleic acid molecule comprising the nucleic acid sequence of SEQ ID NO: 12.

2. An isolated nucleic acid molecule comprising the nucleic acid sequence of SEQ ID NO: 12 operably linked to a coding sequence.

3. The nucleic acid molecule of claim 2, wherein said coding sequence is preceded by the nucleic acid sequence of SEQ ID NO: 12.

4. An expression cassette for expressing a gene in a cell, wherein said cassette comprises operably linked elements comprising a promoter, a leader sequence, and a coding sequence, wherein said leader sequence comprises the nucleic acid sequence of SEQ ID NO: 12.

5. A cell comprising an expression cassette, wherein said cassette comprises operably linked elements comprising a promoter, a leader sequence, and a coding sequence, wherein said leader sequence comprises the nucleic acid sequence of SEQ ID NO: 12.

6. A method for enhancing expression of a gene in a cell, the method comprising expressing an expression cassette in a cell, wherein said cassette comprises operably linked elements comprising a promoter, a leader sequence, and a coding sequence, wherein said leader sequence comprises the nucleic acid sequence of SEQ ID NO: 12.

7. A kit for enhancing expression of a gene in a cell, the kit comprising an isolated nucleic acid molecule comprising the nucleic acid sequence of SEQ ID NO: 12, the kit further comprising an instructional material for the use thereof.

* * * * *

SEQUENCE LISTING

```
<160> NUMBER OF SEQ ID NOS: 12

<210> SEQ ID NO 1
<211> LENGTH: 24
<212> TYPE: DNA
<213> ORGANISM: Artificial sequence
<220> FEATURE:
<223> OTHER INFORMATION: Chemically synthesized

<400> SEQUENCE: 1
```

-continued ggccctgcac attcagactc gagc					24

<210> SEQ ID NO 2
<211> LENGTH: 24
<212> TYPE: DNA
<213> ORGANISM: Artificial sequence
<220> FEATURE:
<223> OTHER INFORMATION: Chemically synthesized

<400> SEQUENCE: 2
ctaggctcga gtctgaatgt gcag					24

<210> SEQ ID NO 3
<211> LENGTH: 20
<212> TYPE: DNA
<213> ORGANISM: Artificial sequence
<220> FEATURE:
<223> OTHER INFORMATION: Chemically synthesized

<400> SEQUENCE: 3
ggggaattgt gagcggataa					20

<210> SEQ ID NO 4
<211> LENGTH: 20
<212> TYPE: DNA
<213> ORGANISM: Artificial sequence
<220> FEATURE:
<223> OTHER INFORMATION: Chemically synthesized

<400> SEQUENCE: 4
gtcgactgaa ttggttccgg					20

<210> SEQ ID NO 5
<211> LENGTH: 20
<212> TYPE: DNA
<213> ORGANISM: Artificial sequence
<220> FEATURE:
<223> OTHER INFORMATION: Chemically synthesized

<400> SEQUENCE: 5
agtggtgata tcaagcttat					20

<210> SEQ ID NO 6
<211> LENGTH: 20
<212> TYPE: DNA
<213> ORGANISM: Artificial sequence
<220> FEATURE:
<223> OTHER INFORMATION: Chemically synthesized

<400> SEQUENCE: 6
tatgctagtt attgctcagc					20

<210> SEQ ID NO 7
<211> LENGTH: 15
<212> TYPE: DNA
<213> ORGANISM: Artificial sequence
<220> FEATURE:
<223> OTHER INFORMATION: Chemically synthesized

<400> SEQUENCE: 7
atggtgagca agggg					15

<210> SEQ ID NO 8
<211> LENGTH: 15
<212> TYPE: DNA
<213> ORGANISM: Artificial sequence

```
<220> FEATURE:
<223> OTHER INFORMATION: Chemically synthesized

<400> SEQUENCE: 8
atggtgagca aggga                                                          15

<210> SEQ ID NO 9
<211> LENGTH: 15
<212> TYPE: DNA
<213> ORGANISM: Artificial sequence
<220> FEATURE:
<223> OTHER INFORMATION: Chemically synthesized

<400> SEQUENCE: 9
atggtgagca agggg                                                          15

<210> SEQ ID NO 10
<211> LENGTH: 15
<212> TYPE: DNA
<213> ORGANISM: Artificial sequence
<220> FEATURE:
<223> OTHER INFORMATION: Chemically synthesized

<400> SEQUENCE: 10
atggtgagca agggg                                                          15

<210> SEQ ID NO 11
<211> LENGTH: 15
<212> TYPE: DNA
<213> ORGANISM: Artificial sequence
<220> FEATURE:
<223> OTHER INFORMATION: Chemically synthesized

<400> SEQUENCE: 11
atggtgagca agggc                                                          15

<210> SEQ ID NO 12
<211> LENGTH: 84
<212> TYPE: DNA
<213> ORGANISM: Artificial sequence
<220> FEATURE:
<223> OTHER INFORMATION: Chemically synthesized

<400> SEQUENCE: 12
atggaattat cacaagtttg tacaaaaaag caggctggcg ccggaaccaa ttcagtcgac          60
tggatccaag aaggagatat aacc                                                84
```